United States Patent
Hall

(10) Patent No.: US 9,969,747 B2
(45) Date of Patent: May 15, 2018

(54) CRYSTALLINE FORMS OF 2-((4S)-6-(4-CHLOROPHENYL)-1-METHYL-4H-BENZO[C]ISOXAZOLO[4,5-E]AZEPIN-4-YL)ACETAMIDE

(71) Applicant: Constellation Pharmaceuticals, Inc., Cambridge, MA (US)

(72) Inventor: Michael L. Hall, Albany, NY (US)

(73) Assignee: Constellation Pharmaceuticals, Inc., Cambridge, MA (US)

(*) Notice: Subject to any disclaimer, the term of this patent is extended or adjusted under 35 U.S.C. 154(b) by 0 days. days.

(21) Appl. No.: 15/319,995

(22) PCT Filed: Jun. 18, 2015

(86) PCT No.: PCT/US2015/036347
§ 371 (c)(1),
(2) Date: Dec. 19, 2016

(87) PCT Pub. No.: WO2015/195862
PCT Pub. Date: Dec. 23, 2015

(65) Prior Publication Data
US 2017/0137434 A1    May 18, 2017

Related U.S. Application Data

(60) Provisional application No. 62/014,782, filed on Jun. 20, 2014.

(51) Int. Cl.
| A61K 31/55 | (2006.01) |
| C07D 498/04 | (2006.01) |
| C07D 491/048 | (2006.01) |

(52) U.S. Cl.
CPC .............. *C07D 491/048* (2013.01)

(58) Field of Classification Search
CPC .............. A61K 31/55; C07D 498/04
USPC .......................... 514/215; 540/578
See application file for complete search history.

(56) References Cited

U.S. PATENT DOCUMENTS

| 3,523,939 A | 8/1970 | Fryer et al. |
| 3,681,343 A | 8/1972 | Hester, Jr. |
| 3,709,898 A | 1/1973 | Hester, Jr. |
| 3,763,144 A | 10/1973 | Hellerback et al. |
| 3,781,289 A | 12/1973 | Hester, Jr. |
| 3,850,942 A | 11/1974 | Hester et al. |
| 3,886,141 A | 5/1975 | Chase |
| 3,903,103 A | 9/1975 | Hester, Jr. |
| 3,966,736 A | 6/1976 | Szmuszkovicz |
| 4,110,455 A | 8/1978 | von Bebenburg et al. |
| 4,155,904 A | 5/1979 | Schlesinger |
| 4,327,026 A | 4/1982 | Branca et al. |
| 4,374,773 A | 2/1983 | Branca et al. |
| 4,377,522 A | 3/1983 | Branca et al. |
| 4,455,307 A | 6/1984 | Hester, Jr. |
| 4,820,834 A | 4/1989 | Evans et al. |
| 4,959,361 A | 9/1990 | Walser |
| 4,992,437 A | 2/1991 | Naka et al. |
| 5,004,741 A | 4/1991 | Evans et al. |
| 5,175,159 A | 12/1992 | Bock et al. |
| 5,185,331 A | 2/1993 | Freidinger et al. |
| 5,185,442 A | 2/1993 | Weber et al. |
| 5,206,234 A | 4/1993 | Bock et al. |
| 5,382,579 A | 1/1995 | Okano et al. |
| 5,409,909 A | 4/1995 | Okano et al. |
| 5,428,004 A | 6/1995 | Earley et al. |
| 5,439,905 A | 8/1995 | Naka et al. |
| 5,550,126 A | 8/1996 | Horwell et al. |
| 5,593,988 A | 1/1997 | Tahara et al. |
| 5,681,833 A | 10/1997 | Castro Pineiro et al. |
| 5,683,998 A | 11/1997 | Shibayama et al. |
| 5,698,552 A | 12/1997 | Weber et al. |
| 5,712,274 A | 1/1998 | Sueoka et al. |
| 5,721,231 A | 2/1998 | Moriwaki et al. |
| 5,733,905 A | 3/1998 | Albright et al. |
| 5,739,129 A | 4/1998 | Aquino et al. |
| 5,753,647 A | 5/1998 | Weber et al. |
| 5,753,649 A | 5/1998 | Tahara et al. |
| 5,760,031 A | 6/1998 | Albright et al. |
| 5,795,887 A | 8/1998 | Aquino et al. |
| 5,840,895 A | 11/1998 | Ohtsuka et al. |
| 5,843,941 A | 12/1998 | Marsters, Jr. et al. |
| 5,869,483 A | 2/1999 | Albright et al. |
| 5,929,069 A | 7/1999 | Shudo |

(Continued)

FOREIGN PATENT DOCUMENTS

| CA | 2020806 A1 | 1/1991 |
| CA | 2032222 A1 | 6/1991 |

(Continued)

OTHER PUBLICATIONS

Brönsted, "Einige Bemerkungen über den Begriff der Säuren und Basen." Recueil des Travaux Chimiques des Pays-Bas. 42(8): 718-28 (1923).
Di Bracco, M., et al., "1,5-Benzodiazepines. Part XII. Synthesis and Biological Evaluations of Tricyclic and Tetracyclic 1,5-benzodiazepine Derivatives as Nevirapine Analogues," European Journal of Medicinal Chemistry, vol. 36, No. 11-12, Dec. 1, 2001, pp. 935-949, XP027205317.
Filippakopoulos, et al., "Selective Inhibition of BET Bromodomains," Nature, Dec. 30, 2010, vol. 468, pp. 1067-1073.
Grey, R., et al., "Structure-Based Design of 3-Aryl-6-Amino-Triazolo[4,3-b] Pyridazine Inhibitors of Pim-1 Kinase," Bioorg. Med, Chem, Lett., vol. 19, No. 11, Jun. 1, 2009, pp. 3019-3022.

(Continued)

*Primary Examiner* — Brenda L Coleman
(74) *Attorney, Agent, or Firm* — McCarter & English, LLP; Steven G. Davis; Michael J. DeGrazia

(57) ABSTRACT

The present disclosure relates to a crystalline form of 2-((4S)-6-(4-chlorophenyl)-1-methyl-4H-benzo[c]isoxazolo[4,5-e]azepin-4-yl)acetamide, which is useful as an inhibitor of bromodomain-containing proteins. The present disclosure also provides pharmaceutically acceptable compositions comprising the crystalline form and methods of using said compositions in the treatment of various disorders.

13 Claims, 12 Drawing Sheets

(56) References Cited

U.S. PATENT DOCUMENTS

| | | |
|---|---|---|
| 6,121,256 A | 9/2000 | Shudo |
| 6,433,167 B1 | 8/2002 | Fujita et al. |
| 6,458,782 B1 | 10/2002 | Kagechika et al. |
| 6,476,017 B2 | 11/2002 | Shudo |
| 6,649,366 B2 | 11/2003 | Chubinskaya et al. |
| 6,777,408 B1 | 8/2004 | Liberatore et al. |
| 7,015,213 B1 | 3/2006 | Bigg et al. |
| 7,160,880 B1 | 1/2007 | Feldman et al. |
| 7,250,410 B2 | 7/2007 | Bourguignon et al. |
| 7,435,730 B2 | 10/2008 | Feldman et al. |
| 7,442,795 B2 | 10/2008 | Bryans et al. |
| 7,473,689 B2 | 1/2009 | Feldman et al. |
| 7,482,337 B2 | 1/2009 | Himmelsbach et al. |
| 7,485,635 B2 | 2/2009 | Feldman et al. |
| 7,528,127 B2 | 5/2009 | Feldman et al. |
| 7,696,212 B2 | 4/2010 | Himmelsbach et al. |
| 8,796,261 B2 * | 8/2014 | Albrecht ............ C07D 498/04 514/215 |
| 9,249,161 B2 | 2/2016 | Albrecht et al. |
| 9,328,117 B2 | 5/2016 | Albrecht et al. |
| 9,422,292 B2 | 8/2016 | Albrecht et al. |
| 9,624,244 B2 | 4/2017 | Albrecht et al. |
| 2001/0039272 A1 | 11/2001 | Shudo |
| 2002/0052358 A1 | 5/2002 | Chubinskaya et al. |
| 2004/0053919 A1 | 3/2004 | Chubinskaya et al. |
| 2004/0138214 A1 | 7/2004 | Himmelsbach et al. |
| 2004/0152888 A1 | 8/2004 | Bourguignon et al. |
| 2006/0128695 A1 | 6/2006 | Bourguignon et al. |
| 2007/0093475 A1 | 4/2007 | Feldman et al. |
| 2007/0105844 A1 | 5/2007 | Glick et al. |
| 2007/0135419 A1 | 6/2007 | Feldman et al. |
| 2007/0135420 A1 | 6/2007 | Feldman et al. |
| 2007/0135421 A1 | 6/2007 | Feldman et al. |
| 2009/0093457 A1 | 4/2009 | Himmelsbach et al. |
| 2010/0041643 A1 | 2/2010 | Adachi et al. |
| 2010/0144703 A1 | 6/2010 | Himmelsbach et al. |
| 2010/0256123 A1 | 10/2010 | Sakuma et al. |
| 2010/0286127 A1 | 11/2010 | Miyoshi et al. |
| 2010/0331316 A1 | 12/2010 | Paoletti et al. |
| 2011/0230460 A1 | 9/2011 | Kempen et al. |
| 2012/0157428 A1 | 6/2012 | Albrecht et al. |
| 2014/0135316 A1 | 5/2014 | Albrecht et al. |

FOREIGN PATENT DOCUMENTS

| | | |
|---|---|---|
| CA | 2032427 A1 | 6/1991 |
| CA | 2050268 A1 | 3/1992 |
| CA | 2056809 A1 | 6/1992 |
| CA | 2059353 A1 | 7/1992 |
| CA | 2062456 A1 | 9/1992 |
| CA | 2071092 A1 | 12/1992 |
| CA | 1327570 C | 3/1994 |
| CA | 02258053 A1 | 12/1997 |
| DE | 2640599 A1 | 3/1978 |
| DE | 3936828 A1 | 5/1990 |
| DE | 4006471 A1 | 9/1990 |
| DE | 4027470 A1 | 3/1992 |
| DE | 4107521 A1 | 9/1992 |
| DE | 4128581 A1 | 3/1993 |
| DE | 4219659 A1 | 12/1993 |
| EP | 0169392 A2 | 1/1986 |
| EP | 0315698 A1 | 5/1989 |
| EP | 0328924 A2 | 8/1989 |
| EP | 0342587 A2 | 11/1989 |
| EP | 0348523 A1 | 1/1990 |
| EP | 0367110 A1 | 5/1990 |
| EP | 0407955 A1 | 1/1991 |
| EP | 0480455 A1 | 4/1992 |
| EP | 495473 A1 | 7/1992 |
| EP | 0514125 A1 | 11/1992 |
| EP | 0559891 A1 | 9/1993 |
| EP | 0656361 A4 | 1/1995 |
| EP | 636625 A2 | 2/1995 |
| EP | 0661284 A4 | 5/1995 |
| EP | 0692483 A4 | 11/1995 |
| EP | 0989131 A1 | 3/2000 |
| EP | 1297836 A1 | 4/2003 |
| EP | 1887008 A1 | 2/2008 |
| EP | 2239264 A1 | 10/2010 |
| FR | 2154511 A1 | 5/1973 |
| FR | 2220257 A1 | 10/1974 |
| GB | 1409693 A | 10/1975 |
| GB | 2259013 A | 3/1993 |
| JP | 7179471 | 7/1995 |
| JP | 11228576 | 8/1999 |
| JP | 2959591 B2 | 10/1999 |
| JP | 03264588 B2 | 3/2002 |
| JP | 03264589 B2 | 3/2002 |
| JP | 04226993 B2 | 2/2009 |
| WO | 9303717 A1 | 3/1993 |
| WO | 9307129 A1 | 4/1993 |
| WO | 9312791 A1 | 7/1993 |
| WO | 9313776 A1 | 7/1993 |
| WO | 9319052 A1 | 9/1993 |
| WO | 9406801 A1 | 3/1994 |
| WO | 9426723 A2 | 11/1994 |
| WO | 9514694 A1 | 6/1995 |
| WO | 9528399 A1 | 10/1995 |
| WO | 9711061 A1 | 3/1997 |
| WO | 9747622 A1 | 12/1997 |
| WO | 9811111 A1 | 3/1998 |
| WO | 9828268 A2 | 7/1998 |
| WO | 9858930 A1 | 12/1998 |
| WO | 199929324 A1 | 6/1999 |
| WO | 200006157 A1 | 2/2000 |
| WO | 2000012547 A2 | 3/2000 |
| WO | 0054778 A1 | 9/2000 |
| WO | 2000069836 A1 | 11/2000 |
| WO | 2001047510 A2 | 7/2001 |
| WO | 2002098865 A2 | 12/2002 |
| WO | 2003074525 A1 | 9/2003 |
| WO | 2004041258 A2 | 5/2004 |
| WO | 2004041820 A1 | 5/2004 |
| WO | 2004058769 A2 | 7/2004 |
| WO | 2005002590 A1 | 1/2005 |
| WO | 2005099759 A1 | 10/2005 |
| WO | 0638560 A1 | 4/2006 |
| WO | 2006129623 A1 | 12/2006 |
| WO | 2007016087 A2 | 2/2007 |
| WO | 2007050587 A2 | 5/2007 |
| WO | 2007079820 A1 | 7/2007 |
| WO | 2008023847 A1 | 2/2008 |
| WO | 2008109856 A2 | 9/2008 |
| WO | 2009059191 A1 | 5/2009 |
| WO | 2009081349 A1 | 7/2009 |
| WO | 2009152589 A1 | 12/2009 |
| WO | 2010008459 A1 | 1/2010 |
| WO | 2010049466 A1 | 5/2010 |
| WO | 2010121164 A2 | 10/2010 |
| WO | 2010128685 A1 | 11/2010 |
| WO | 2011037128 A1 | 3/2011 |
| WO | 2011054553 A1 | 5/2011 |
| WO | 2011054841 A1 | 5/2011 |
| WO | 2011054843 A1 | 5/2011 |
| WO | 2011054844 A1 | 5/2011 |
| WO | 2011054845 A1 | 5/2011 |
| WO | 2011054846 A1 | 5/2011 |
| WO | 2011054848 A1 | 5/2011 |
| WO | 2011054851 A1 | 5/2011 |
| WO | 2011079315 A1 | 6/2011 |
| WO | 2011123678 A1 | 10/2011 |
| WO | 2011143651 A1 | 11/2011 |
| WO | 2011143657 A1 | 11/2011 |
| WO | 2011143660 A2 | 11/2011 |
| WO | 2011143669 A2 | 11/2011 |
| WO | 2011161031 A1 | 12/2011 |
| WO | 2012075383 A2 | 6/2012 |
| WO | 2013024104 A1 | 2/2013 |
| WO | 2013030150 A1 | 3/2013 |
| WO | 2013033268 A2 | 3/2013 |
| WO | 2013033269 A1 | 3/2013 |
| WO | 2013033270 A2 | 3/2013 |
| WO | 2013033420 A1 | 3/2013 |

(56) References Cited

FOREIGN PATENT DOCUMENTS

| WO | 2013130573 A1 | 9/2013 |
|---|---|---|
| WO | 2013155317 A1 | 10/2013 |
| WO | 2013159006 A1 | 10/2013 |

OTHER PUBLICATIONS

Gussio, Rick, et al., "All-Atom Models for the Non-Nucleoside Binding Site of HIV-1 Reverse Transcriptase Complexed with Inhibitors: A 3D QSAR Approach," J. Med. Chem., Apr. 12, 1996, vol. 39, No. 8, pp. 1645-1650.

Hancock et al. "What is the true solubility advantage for amorphous pharmaceuticals?" Pharm Res. 17(4):397-404 (2000).

International Preliminary Report on Patentability, dated Nov. 5, 2013, Int'l Appl'n No. PCT/US2012/036569, Int'l Filing Date May 4, 2012.

International Preliminary Report on Patentability, dated Jan. 3, 2014, International Application No. PCT/US2012/042825; International Filing Date: Jun. 15, 2012, 10 pages.

International Search Report and Written Opinion, dated Apr. 17, 2012, Int'l Appl'n No. PCT/US2011/063173, Int'l Filing Date Dec. 2, 2011.

International Search Report and Written Opinion, dated Feb. 21, 2013, Int'l Appl'n No. PCT/US2012/042825, Int'l Filing Date Jun. 15, 2012.

International Search Report and Written Opinion, dated Jul. 23, 2013, Int'l Appl'n No. PCT/US2013/044444, Int'l Filing Date Jun. 6, 2013.

International Search Report and Written Opinion, dated Jul. 23, 2013, Int'l Appl'n No. PCT/US2013/044449, Int'l Filing Date Jun. 6, 2013.

Jiban K. Chakrabarti, et al., "Chemistry of Adamantane. Part XI. 1,2-Disubstituted Adamantanes. Synthesis and Reactions of Adamantano[2,1-b ]- and protoadamantano-[4,5-b ] [1,5]benzodiazepines," Journal of Heterocyclic Chemistry, vol. 15, No. 5, Aug. 1, 1978, pp. 705-710, XP055136791.

Konno, "Physical and chemical changes of medicinals in mixtures with adsorbents in the solid state. IV. Study on reduced-pressure mixing for practical use of amorphous mixtures of flufenamic acid." Chem Pharm Bull (Tokyo). 38(7):2003-7 (1990).

Kosychova, et al., "Synthesis of New [1,2,4]triazolo[4,3-a][1,5]benzodiaze-pine derivatives," Lietuvos Mokslu Akademija. Chemija, vol. 22, No. 1, Jan. 1, 2011, pp. 60-64, XP055136653.

Kosychova, et al., "Synthesis of novel 5,6-dihydro-4H-[1,2,4]triazolo[4,3-a][1,5]benzodiazepines," Rigas Tehniskas Universitates Zinatniskie Raksti. Serija 1: Materialzinatne Un Lietiska Kimija, vol. 22, Jan. 1, 2010, pp. 94-99, XP009179817.

Kosychova, L., et al., "Synthesis of Substitute 5,6-Dihydro-4H-[1,2,4]Triazolo[4,3-a][1,5]Benzodiazepines," Chemistry of Heterocyclic Compounds, vol. 40, No. 6, Jun. 2004, pp. 811-815.

Law et al. "Ritonavir-PEG 8000 amorphous solid dispersions: in vitro and in vivo evaluations." J Pharm Sci. 93(3):563-70 (2004).

Proctor, George R., et al., "Azabenzycycloheptones, Part 19, Formation of Some Heterocyclic Annulated Compounds from 1,2,3,4-tetrahydro-1-benzazepine derivatives," Journal of the Chemical Society, Perkin Transactions 1, Chemical Society, Letchworth, GB, Jan. 1, 1978, pp. 862-879.

Szarvasi, E., et al., "(4H)Dihydro-5,6(s)-triazolo-(4,3-a)benzodiazepines-1,5 a activite analgesique et anti-inflammatoire," European Journal of Medicinal Chemistry, vol. 13, No. 2, Mar. 1, 1978, pp. 113-119, XP009179828.

Terrell, N.K., et al., "Imidazoú2',3':6,5 3/4 Dipyridoú3,2-B:2',3'-E 3/4-1,4-Diazepines: Non-Nucleoside HIV-1 Reverse Transcriptase Inhibitors with Greater Enzyme Affinity than Nevirapine," Bioorganic & Medicinal Chemistry Letters, vol. 12, No. 2, Dec. 1, 1992, pp. 1745-1750, XP002912883.

Venkateswarlu, Peesapati, et al., "Synthesis and Biological Activity of Some New Heterocyclic Annelated Compounds from 2,3,4,5-tetrahydro-1-benzazepines," Indian Journal of Chemistry: IJC, Council of Scientific and Industrial Research, IN., vol. 35B, Dec. 1, 1996, pp. 1287-1293.

U.S. Appl. No. 13/309,646, filed Dec. 2, 2011, U.S. Pat. No. 8,796,261.

U.S. Appl. No. 14/313,148, filed Jun. 24, 2014, U.S. Pat. No. 9,522,920.

U.S. Appl. No. 15/346,048, filed Nov. 9, 2016.

U.S. Appl. No. 14/405,209, filed Dec. 3, 2014, U.S. Pat. No. 9,493,483.

U.S. Appl. No. 15/277,854, filed Sep. 27, 2016.

\* cited by examiner

CRYSTALLINE FORMS OF 2-((4S)-6-(4-CHLOROPHENYL)-1-METHYL-4H-BENZO[C]ISOXAZOLO[4,5-E]AZEPIN-4-YL)ACETAMIDE

RELATED APPLICATIONS

This application is a 35 U.S.C. § 371 national stage filing of International Application No. PCT/US2015/036347, filed Jun. 18, 2015, which in turn claims the benefit of U.S. Provisional Application No. 62/014,782, filed Jun. 20, 2014, the entire contents of each of which are incorporated herein by reference.

TECHNICAL FIELD OF THE INVENTION

Provided herein is crystalline Form A of 2-((4S)-6-(4-chlorophenyl)-1-methyl-4H-benzo[c]isoxazolo[4,5-e]azepin-4-yl)acetamide, processes for the preparing the crystalline form, pharmaceutical compositions comprising the crystalline form, and uses of the crystalline form and compositions thereof in treating bromodomain-containing protein-mediated disorders.

BACKGROUND OF THE INVENTION

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin: the defining template for gene regulation. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding proteins or chromatin-modifying enzymes. Significantly, an increasing number of these proteins have been associated with a variety of disorders such as neurodegenerative disorders, metabolic diseases, inflammation, and cancer. Thus, highly selective therapeutic agents directed against this emerging class of gene regulatory proteins promise new approaches to the treatment of human diseases.

2-((4S)-6-(4-chlorophenyl)-1-methyl-4H-benzo[c]isoxazolo[4,5-e]azepin-4-yl)acetamide is an inhibitor of one or more bromodomain-containing proteins and is useful in treating bromodomain-containing protein-mediated disorders, such as, e.g., proliferative disorders, inflammatory diseases, sepsis, autoimmune diseases, and viral infections. The amorphous form of 2-((4S)-6-(4-chlorophenyl)-1-methyl-4H-benzo[c]isoxazolo[4,5-e]azepin-4-yl)acetamide is exemplified in U.S. Patent Publication No. 2012/0157428 as Compound 144, and is incorporated herein by reference. 2-((4S)-6-(4-chlorophenyl)-1-methyl-4H-benzo[c]isoxazolo[4,5-e]azepin-4-yl)acetamide is represented by the following structural formula:

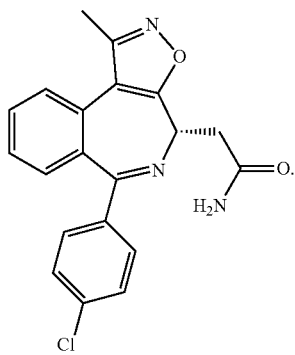 [SMILES: Cc1noc2c1-c1ccccc1C(c1ccc(Cl)cc1)=N[C@H]2CC(N)=O]

Given the therapeutic benefits associated with the amorphous form of 2-((4S)-6-(4-chlorophenyl)-1-methyl-4H-benzo[c]isoxazolo[4,5-e]azepin-4-yl)acetamide, development of other forms of this compound, having improved properties, represents an attractive area for producing enhanced formulations for inhibition of one or more bromodomain-containing proteins.

SUMMARY OF THE INVENTION

Provided herein is a novel crystalline Form A of 2-((4S)-6-(4-chlorophenyl)-1-methyl-4H-benzo[c]isoxazolo[4,5-e]azepin-4-yl)acetamide, which has improved properties and displays advantageous characteristics over the prior disclosed amorphous form. As described in detail below, such advantages include e.g., improved relative humidity stability, ease of isolation, favorable pharmacokinetic parameters, and process reproducibility of 2-((4S)-6-(4-chlorophenyl)-1-methyl-4H-benzo[c]isoxazolo[4,5-e]azepin-4-yl)acetamide.

Also provided herein is a novel hydrated (e.g., monohydrate) crystalline Form A of 2-((4S)-6-(4-chlorophenyl)-1-methyl-4H-benzo[c]isoxazolo[4,5-e]azepin-4-yl)acetamide.

Further provided herein are pharmaceutical compositions comprising crystalline and hydrated crystalline Form A of 2-((4S)-6-(4-chlorophenyl)-1-methyl-4H-benzo[c]isoxazolo[4,5-e]azepin-4-yl)acetamide, methods for their manufacture, and uses thereof for treating bromodomain-containing protein-mediated disorders, such as, e.g., proliferative disorders, inflammatory diseases, sepsis, autoimmune diseases, and viral infections.

DETAILED DESCRIPTION

Definitions

Figure 1:
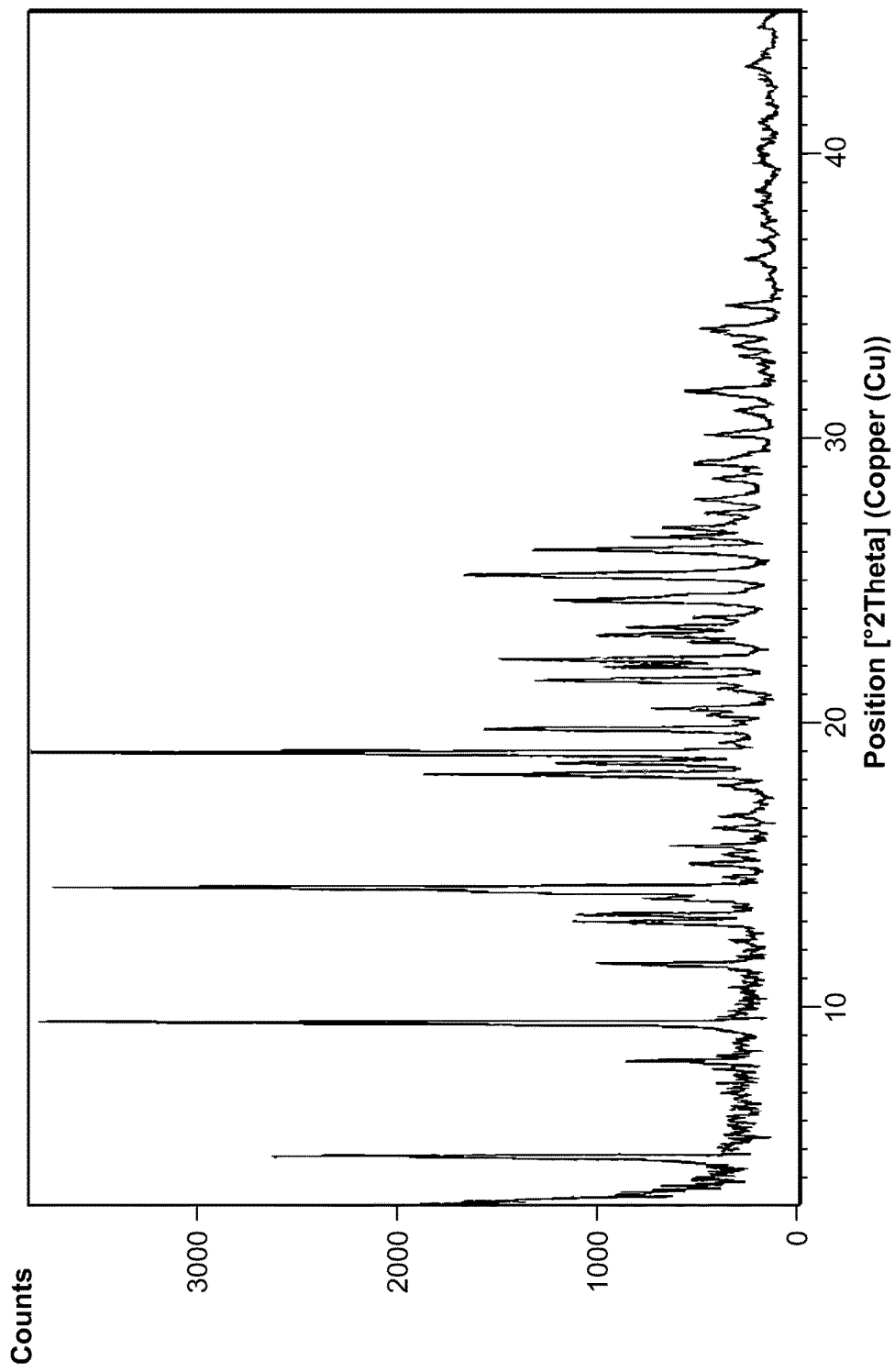
FIG. 1 depicts an X-ray powder diffraction pattern (XRPD) for monohydrate crystalline Form A of 2-((4S)-6-(4-chlorophenyl)-1-methyl-4H-benzo[c]isoxazolo[4,5-e]azepin-4-yl)acetamide.

When used alone, the term "Form A" refers to the crystalline polymorph Form A of 2-((4S)-6-(4-chlorophenyl)-1-methyl-4H-benzo[c]isoxazolo[4,5-e]azepin-4-yl)acetamide. The terms "Form A", "Form A of 2-((4S)-6-(4-chlorophenyl)-1-methyl-4H-benzo[c]isoxazolo[4,5-e]azepin-4-yl)acetamide", and "crystalline Form A of 2-((4S)-6-(4-chlorophenyl)-1-methyl-4H-benzo[c]isoxazolo[4,5-e]azepin-4-yl)acetamide" are used interchangeably. The terms "Form A", "Form A of 2-((4S)-6-(4-chlorophenyl)-1-methyl-4H-benzo[c]isoxazolo[4,5-e]azepin-4-yl)acetamide", and "crystalline Form A of 2-((4S)-6-(4-chlorophenyl)-1-methyl-4H-benzo[c]isoxazolo[4,5-e]azepin-4-yl)acetamide" are intended to include hydrated and solvated forms of the crystalline polymorph Form A of 2-((4S)-6-(4-chlorophenyl)-1-methyl-4H-benzo[c]isoxazolo[4,5-e]azepin-4-yl)acetamide as well as anhydrous forms. Such forms are characterized e.g., by XRPD. "Anhydrous" as used herein, means that the crystalline form comprises substantially no water in the crystal lattice e.g., less than 1% by weight as determined by Karl Fisher analysis.

When used alone, the term "monohydrate Form A" refers to the monohydrate crystalline polymorph Form A of 2-((4S)-6-(4-chlorophenyl)-1-methyl-4H-benzo[c]isoxazolo[4,5-e]azepin-4-yl)acetamide. The terms "monohydrate Form A", "monohydrate crystalline Form A", and "monohydrate crystalline Form A of 2-((4S)-6-(4-chlorophenyl)-1-methyl-4H-benzo[c]isoxazolo[4,5-e]azepin-4-yl)acetamide are used interchangeably. Monohydrate Form A is characterized e.g., by XRPD together with Karl Fisher titration analysis.

The term "amorphous" means a solid that is present in a non-crystalline state or form. Amorphous solids are disordered arrangements of molecules and therefore possess no distinguishable crystal lattice or unit cell and consequently have no definable long range ordering. Solid state ordering of solids may be determined by standard techniques known in the art, e.g., by X-ray powder diffraction (XRPD) or differential scanning calorimetry (DSC). Amorphous solids can also be differentiated from crystalline solids e.g., by birefringence using polarized light microscopy.

The term "pharmaceutically acceptable carrier, adjuvant, or vehicle" refers to a non-toxic carrier, adjuvant, or vehicle that does not adversely affect the pharmacological activity of the compound with which it is formulated, and which is also safe for human use. Pharmaceutically acceptable carriers, adjuvants or vehicles that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

Description of Exemplary Compounds

In one aspect, the present disclosure provides crystalline Form A of 2-((4S)-6-(4-chlorophenyl)-1-methyl-4H-benzo[c]isoxazolo[4,5-e]azepin-4-yl)acetamide.

In one aspect, crystalline Form A of 2-((4S)-6-(4-chlorophenyl)-1-methyl-4H-benzo[c]isoxazolo[4,5-e]azepin-4-yl)acetamide is characterized by at least three, at least four, at least five, or by six x-ray powder diffraction peaks at 2Θ angles selected from 4.73°, 18.09°, 18.48°, 18.80°, 19.70°, and 25.17°. Alternatively, crystalline Form A is characterized by x-ray powder diffraction peaks at 2Θ angles 4.73°, 9.42°, 12.91°, 18.09°, 18.48°, 18.80°, 19.70°, 21.42°, and 25.17°. In another alternative crystalline Form A is characterized by x-ray powder diffraction peaks at 2Θ angles 4.73°, 8.11°, 9.42°, 12.91°, 14.10°, 14.97°, 18.09°, 18.48°, 18.80°, 19.70°, 21.42°, and 25.17°, 26.07°, and 26.53°.

In another aspect, crystalline Form A of 2-((4S)-6-(4-chlorophenyl)-1-methyl-4H-benzo[c]isoxazolo[4,5-e]azepin-4-yl)acetamide has an XRPD pattern that is substantially the same XRPD pattern shown in FIG. 1.

Figure 10:
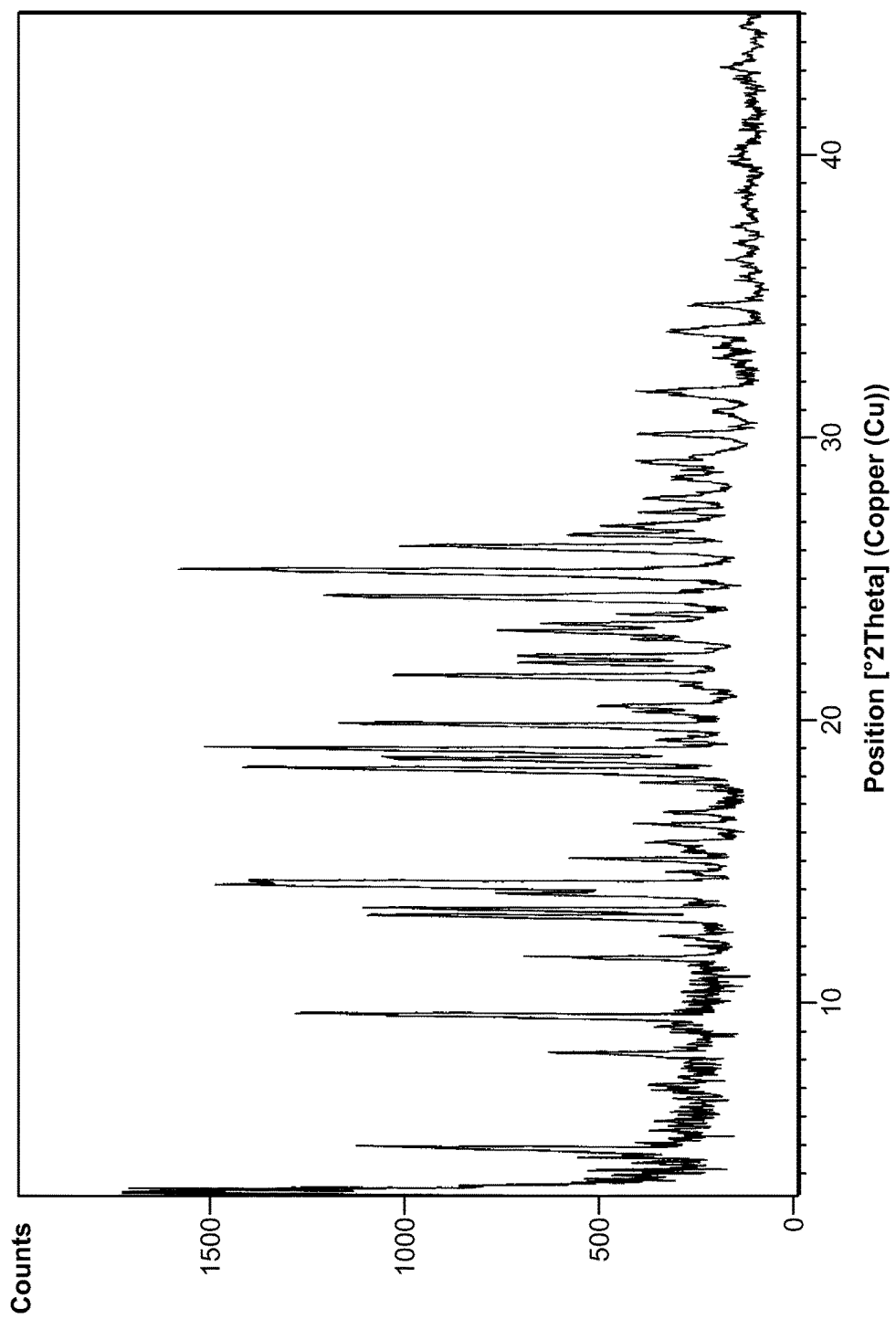
FIG. 10 depicts an X-ray powder diffraction pattern (XRPD) for GMP scale up of monohydrate crystalline Form A of 2-((4S)-6-(4-chlorophenyl)-1-methyl-4H-benzo[c]isoxazolo[4,5-e]azepin-4-yl)acetamide.

In another aspect, crystalline Form A of 2-((4S)-6-(4-chlorophenyl)-1-methyl-4H-benzo[c]isoxazolo[4,5-e]azepin-4-yl)acetamide has an XRPD pattern that is substantially the same XRPD pattern shown in FIG. 10.

In another aspect, crystalline Form A of 2-((4S)-6-(4-chlorophenyl)-1-methyl-4H-benzo[c]isoxazolo[4,5-e]azepin-4-yl)acetamide has an XRPD pattern that substantially includes the peaks in Table 2.

In another aspect, crystalline Form A of 2-((4S)-6-(4-chlorophenyl)-1-methyl-4H-benzo[c]isoxazolo[4,5-e]azepin-4-yl)acetamide has an XRPD pattern that substantially includes the peaks in Table 3.

In another aspect, crystalline Form A of 2-((4S)-6-(4-chlorophenyl)-1-methyl-4H-benzo[c]isoxazolo[4,5-e]azepin-4-yl)acetamide is characterized by 13C-NMR peaks at 171.3, 168.6, 167.4, 139.30, 134.7, 133.4, 131.4, 131.1, 130.7, 130.0, 128.0, 126.8, 125.8, 112.55, 55.9, 53.5, 36.4, 18.5, and 10.6 in DMSO-$d_6$ with 0.05% tetramethylsilane.

Figure 2:
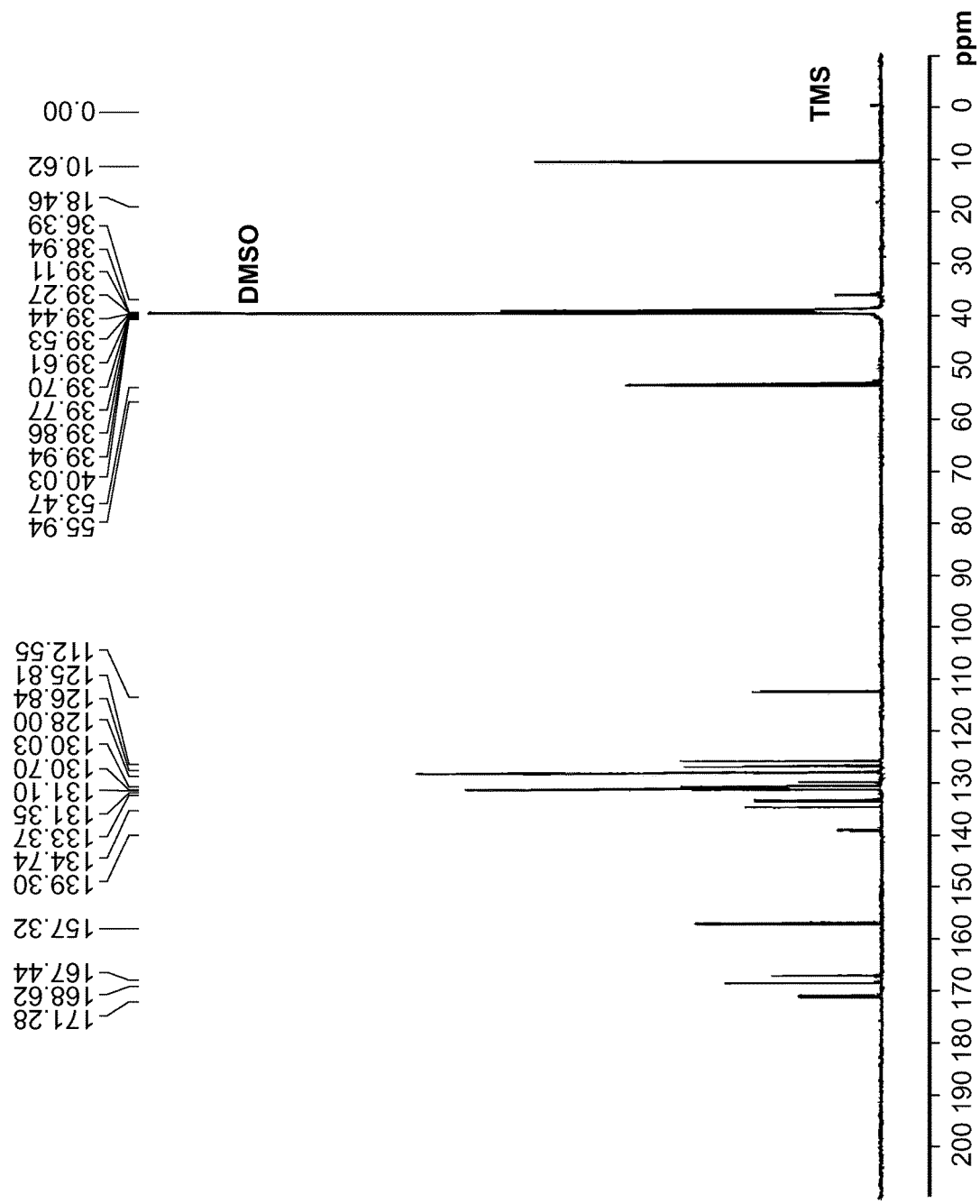
FIG. 2 depicts a 13C-NMR profile for monohydrate crystalline Form A of 2-((4S)-6-(4-chlorophenyl)-1-methyl-4H-benzo[c]isoxazolo[4,5-e]azepin-4-yl)acetamide.

Alternatively, crystalline Form A is characterized by a 13C-NMR pattern that is substantially the same 13C-NMR pattern shown in FIG. 2.

Figure 3:
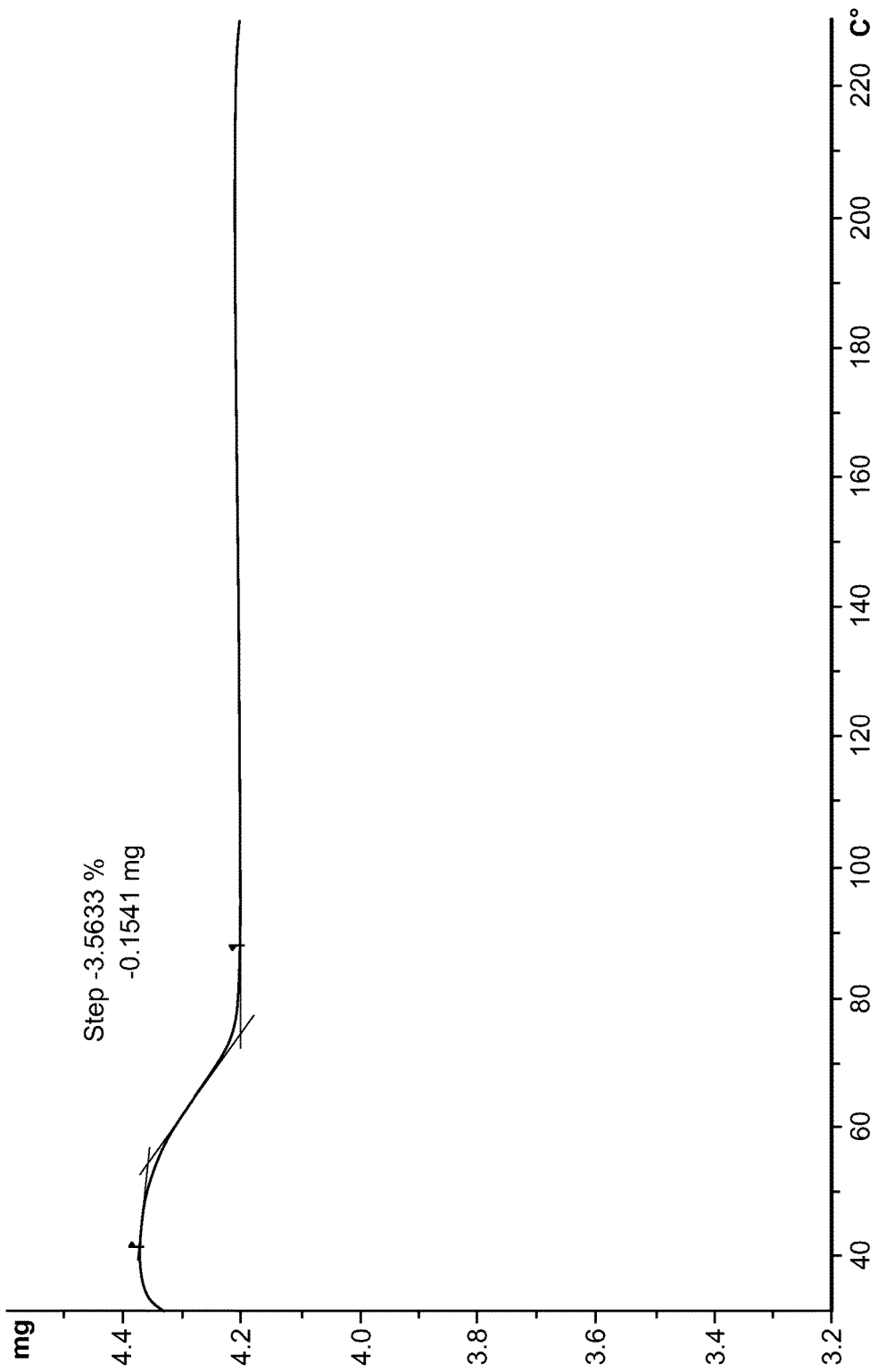
FIG. 3 depicts a thermal gravimetric analysis (TGA) pattern for monohydrate crystalline Form A of 2-((4S)-6-(4-chlorophenyl)-1-methyl-4H-benzo[c]isoxazolo[4,5-e]azepin-4-yl)acetamide.

In one aspect, crystalline Form A of 2-((4S)-6-(4-chlorophenyl)-1-methyl-4H-benzo[c]isoxazolo[4,5-e]azepin-4-yl) acetamide has a TGA pattern that is substantially the same TGA pattern shown in FIG. 3. Alternatively, crystalline Form A of 2-((4S)-6-(4-chlorophenyl)-1-methyl-4H-benzo [c]isoxazolo[4,5-e]azepin-4-yl)acetamide has a TGA pattern that is substantially the same TGA pattern shown in FIG. 12.

Figure 5:
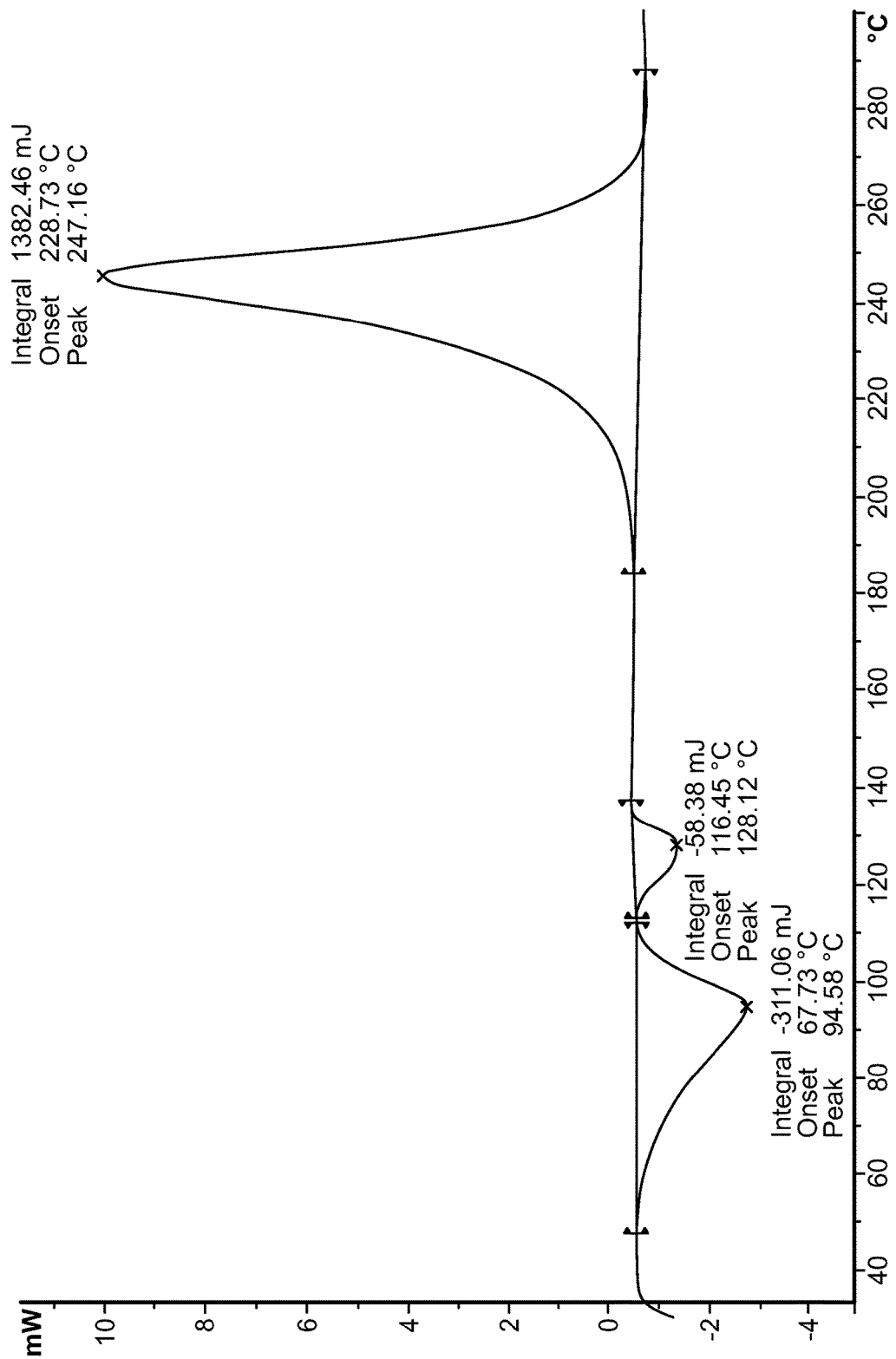
FIG. 5 depicts a Differential Scanning calorimetry (DSC) spectrum for monohydrate crystalline Form A of 2-((4S)-6-(4-chlorophenyl)-1-methyl-4H-benzo[c]isoxazolo[4,5-e]azepin-4-yl)acetamide.

In one aspect, crystalline Form A of 2-((4S)-6-(4-chlorophenyl)-1-methyl-4H-benzo[c]isoxazolo[4,5-e]azepin-4-yl) acetamide has a DSC pattern that is substantially the same DSC pattern shown in FIG. 5. Alternatively, crystalline Form A of 2-((4S)-6-(4-chlorophenyl)-1-methyl-4H-benzo [c]isoxazolo[4,5-e]azepin-4-yl)acetamide has a DSC pattern that is substantially the same DSC pattern shown in FIG. 11.

In one aspect, the crystalline forms recited in the preceeding paragraphs represent a hydrated crystalline Form A (e.g., monohohydrate Form A) of 2-((4S)-6-(4-chlorophenyl)-1-methyl-4H-benzo[c]isoxazolo[4,5-e]azepin-4-yl)acetamide.

In one aspect, the hydrated crystalline Form A of 2-((4S)-6-(4-chlorophenyl)-1-methyl-4H-benzo[c]isoxazolo[4,5-e]azepin-4-yl)acetamide is a monohydrate characterized by by at least three, at least four, at least five, or by six x-ray powder diffraction peaks at 2Θ angles selected from 4.73°, 18.09°, 18.48°, 18.80°, 19.70°, and 25.17°; optionally together with one or both of the TGA and DSC parameters recited above; and a Karl Fisher titration water composition range of 4 to 5 wt %.

It will be understood that the 2-theta values of the X-ray powder diffraction patterns for monohydrate crystalline Form A may vary slightly from one instrument to another and also depending on variations in sample preparation and batch to batch variation. For example, without wishing to be bound by theory, it is believed that some variations in 2-theta values are attributable to the amount of water comprised in the crystalline lattice, e.g., in the case of hydrated (such as a monohydrate) and anhydrous forms. Therefore, the XRPD patterns/assignments for crystalline Form A are not to be construed as absolute and can vary ±0.2 degrees, except for the 2Θ angles 8.11°, 14.10°, 14.97°, 26.07°, and 26.53° of crystalline Form A, which can vary by ±0.3 degrees.

As intended herein, "substantially the same XRPD pattern as shown in FIG. 1" and ""substantially the same XRPD pattern as shown in FIG. 10" means that for comparison purposes, at least 90% of the peaks shown in FIG. 1 and FIG. 10 are present. It is to be further understood that for comparison purposes some variability in peak intensities from those shown in FIG. 1 and FIG. 10 are allowed, such as ±0.2 degrees, except for the 2Θ angles 8.11°, 14.10°, 14.97°, 26.07°, and 26.53° of crystalline Form A, which can vary by ±0.3 degrees.

It will also be understood that the chemical shifts of the NMR patterns for the monohydrate crystalline Form A may vary slightly from one instrument to another and also depending on variations in sample preparation and batch to batch variation. Therefore, the NMR chemical shifts, patterns, and/or assignments for monohydrate crystalline Form A are not to be construed as absolute and can vary±0.2 ppm.

In one aspect, the present disclosure provides a process for preparing crystalline Form A of 2-((4S)-6-(4-chlorophenyl)-1-methyl-4H-benzo[c]isoxazolo[4,5-e]azepin-4-yl)acetamide. Such a process includes, e.g., forming crystalline Form A from a solution comprising amorphous 2-((4S)-6-(4-chlorophenyl)-1-methyl-4H-benzo[c]isoxazolo[4,5-e]azepin-4-yl)acetamide and water; or forming crystalline Form A from a solution comprising amorphous 2-((4S)-6-(4-chlorophenyl)-1-methyl-4H-benzo[c]isoxazolo[4,5-e]azepin-4-yl)acetamide and a combination of water and organic solvent. In one aspect, crystalline Form A is precipitated from a solution comprising amorphous 2-((4S)-6-(4-chlorophenyl)-1-methyl-4H-benzo[c]isoxazolo[4,5-e]azepin-4-yl)acetamide and a combination of water and organic solvent. In one aspect, the processes described above results in the formation of monohydrate crystalline Form A.

Acceptable solvent mixtures for the aforementioned processes include, e.g., ethanol/water, isopropanol/water, tetrahydrofuran/water, acetone/water, methanol/water, and acetonitrile/water. In one aspect, the process described herein comprises formation of monohydrate crystalline Form A from amorphous 2-((4S)-6-(4-chlorophenyl)-1-methyl-4H-benzo[c]isoxazolo[4,5-e]azepin-4-yl)acetamidee in a 60:40 mixture of ethanol/water.

Processes for preparing crystalline Form A also include seeding a solution comprising amorphous 2-((4S)-6-(4-chlorophenyl)-1-methyl-4H-benzo[c]isoxazolo[4,5-e]azepin-4-yl)acetamide and water with crystalline Form A of 2-((4S)-6-(4-chlorophenyl)-1-methyl-4H-benzo[c]isoxazolo[4,5-e]azepin-4-yl)acetamide; or seeding a solution comprising amorphous 2-((4S)-6-(4-chlorophenyl)-1-methyl-4H-benzo [c]isoxazolo[4,5-e]azepin-4-yl)acetamide and a combination of water and organic solvent with crystalline Form A of 2-((4S)-6-(4-chlorophenyl)-1-methyl-4H-benzo[c]isoxazolo [4,5-e]azepin-4-yl)acetamide. In one aspect, the seeding is done with monohydrate crystalline Form A to prepare the resulting monohydrate form. Processes for preparing crystalline Form A and the specific monohydrate crystalline Form A can also be achieved upon suspending amorphous 2-((4S)-6-(4-chlorophenyl)-1-methyl-4H-benzo[c]isoxazolo [4,5-e]azepin-4-yl)acetamide in water, absent seeding.

Acceptable solvent mixtures for the process mention in the two preceding paragraphs also include, e.g., ethanol/water, isopropanol/water, tetrahydrofuran/water, acetone/water, methanol/water, and acetonitrile/water. In one aspect, the process described herein comprises formation of monohydrate crystalline Form A from seeding amorphous 2-((4S)-6-(4-chlorophenyl)-1-methyl-4H-benzo[c]isoxazolo[4,5-e]azepin-4-yl)acetamide with crystalline monohydrate Form A of 2-((4S)-6-(4-chlorophenyl)-1-methyl-4H-benzo[c]isoxazolo[4,5-e]azepin-4-yl)acetamide in a 60:40 mixture of ethanol/water.

Uses, Formulation and Administration

Pharmaceutically Acceptable Compositions

According to other aspects, the present disclosure relates to a method of inhibiting a bromodomain-containing protein (such as a BET protein, e.g., BRD2, BRD3, BRD4, and/or BRDT) using a composition comprising crystalline Form A described herein and a pharmaceutically acceptable carrier, adjuvant, or vehicle. The amount of the crystalline form in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain aspects, the amount of the crystalline form in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain aspects, a provided composition is formulated for administration to a patient in need of such composition. In some aspects, a provided composition is formulated for oral administration to a patient.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Other forms of administration are as described in U.S. Patent Publication No. 2012/0157428. Dosage forms for oral administration are also as described in U.S. Patent Publication No. 2012/0157428, the contents of which are incorporated herein by reference.

The amount of provided crystalline form that may be combined with carrier materials to produce a composition in a single dosage form will vary depending upon the patient to be treated and the particular mode of administration. Provided compositions may be formulated such that a dosage of between 0.001-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided crystalline form in the composition will also depend upon the particular compound in the composition.

Uses of Compounds and Pharmaceutically Acceptable Compositions

Crystalline Form A of 2-((4S)-6-(4-chlorophenyl)-1-methyl-4H-benzo[c]isoxazolo[4,5-e]azepin-4-yl)acetamide and compositions described herein are generally useful for the inhibition of activity of one or more proteins involved in epigenetic regulation e.g., as those described in U.S. Patent Publication No. 2012/0157428. Thus, in some aspects, the present disclosure provides a method of inhibiting one or more proteins involved in epigenetic regulation, such as proteins containing acetyl-lysine recognition motifs, also known as bromodomains (e.g., BET proteins, such as BRD2, BRD3, BRD4, and/or BRDT), by administering a provided crystalline form or composition.

The present disclosure also relates to treating MYC-dependent cancers, inflammatory diseases, and viral diseases (e.g., as those described in U.S. Patent Publication No. 2012/0157428), comprising administering one or more of the compounds described herein.

As used herein, the terms "treatment," "treat," and "treating" refer to reversing, alleviating, or inhibiting the progress of a disease or disorder, or one or more symptoms thereof, as described herein.

Diseases and conditions treatable according to the methods described herein include, but are not limited to, cancer and other proliferative disorders, inflammatory diseases, sepsis, autoimmune disease, and viral infection. Thus, one aspect is a method of treating a subject having a disease, disorder, or symptom thereof the method including administration of a crystalline form or composition herein to the subject. In one aspect, a human patient is treated with a crystalline form described herein and a pharmaceutically acceptable carrier, adjuvant, or vehicle, wherein said crystalline form is present in an amount to measurably inhibit bromodomain-containing protein activity (such as BET protein, e.g., BRD2, BRD3, BRD4, and/or BRDT) in the patient.

The present disclosure further relates to a method for treating or ameliorating cancer or another proliferative disorder by administration of an effective amount of a crystalline form as described herein to a mammal, in particular a human in need of such treatment. In some aspects, the disease to be treated is cancer. Examples of cancers treated include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In some aspects, the present disclosure provides a method of treating a benign proliferative disorders, infectious and noninfectious inflammatory events and autoimmune and other inflammatory diseases, systemic inflammatory response syndromes, and viral infections, e.g., those as described in U.S. Patent Publication No. 2012/0157428.

The present disclosure further provides a method of treating a subject, such as a human, suffering from one of the abovementioned conditions, illnesses, disorders or diseases. The method comprises administering a therapeutically effective amount of crystalline Form A, which functions by inhibiting a bromodomain and, in general, by modulating gene expression, to induce various cellular effects, in particular induction or repression of gene expression, arresting cell proliferation, inducing cell differentiation and/or inducing apoptosis, to a subject in need of such treatment.

The present disclosure further relates to the use of a provided crystalline form for the production of pharmaceutical compositions which are employed for the treatment and/or amelioration of the diseases, disorders, illnesses and/or conditions as mentioned herein.

Another aspect of the present disclosure is the use of the crystalline form as described herein in the manufacture of a medicament for use in the treatment of a disorder or disease herein. Another object of the present disclosure is the use of the crystalline form as described herein for use in the treatment of a disorder or disease herein.

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

The disclosed crystalline form may also be used in combination with one or more antiproliferative compounds or other additional compounds, e.g., as described in U.S. Patent Publication No. 2012/0157428, the contents of which are incorporated herein by reference.

As used herein, the term "combination," "combined," and related terms refers to the simultaneous or sequential administration of therapeutic agents in accordance with the present disclosure. For example, a provided crystalline form may be administered with another therapeutic agent simultaneously or sequentially in separate unit dosage forms or together in a single unit dosage form. Accordingly, one aspect provides a single unit dosage form comprising a provided crystalline form, an additional therapeutic agent, and a pharmaceutically acceptable carrier, adjuvant, or vehicle for use in the methods of the disclosure.

Exemplification

As depicted in the Examples below, in certain exemplary embodiments, crystalline Form A is prepared according to the following general procedures.

XRPD analyses were conducted using a CubiX-Pro XRD operating with a Cu radiation source at 45 kV, 40 mA. Samples were placed on Si zero-return sample holders and analysis was performed using a 10 mm irradiated width. The scanning parameters were from a range of 3.0 to 45.0° with a step size of 0.02°, 10 seconds per step, and an active length of 2.54°. Peak assignments were performed using X'Pert HighScore Plus software with the following parameters: Fixed Divergence Slit Size, 1.00°, 1.59 mm and Crossover Point, 44.3° Omega.

Differential Scanning calorimetry was performed on a Mettler $822^e$ on the sample "as is." Sample were weighed in an aluminum pan, covered with a pierced lid, and then crimped and analyzed from 30 to 300° C. ramped at 10° C./min.

Thermal Gravimetric Analysis was performed on a Mettler $851^e$ SDTA/TGA on the sample "as is." Samples were weighed in an alumina crucible and analyzed from 30 to 300° C. at 10° C./min.

Nuclear Magnetic Resonance was performed on a 500 MHz Bruker AVANCE. Samples were dissolved in DMSO-$d_6$ with 0.05% tetramethylsilane for internal reference.

Determination of water content (Karl Fisher analysis) was performed as per USP <921>, method IC (coulometric titration). Samples were used as-is and hydranal-coulomat AD was used at the titrant.

Preparation of Monohydrate Crystalline Form A of 2-((4S)-6-(4-chlorophenyl)-1-methyl-4H-benzo[c]isoxazolo[4,5-e]azepin-4-yl)acetamide

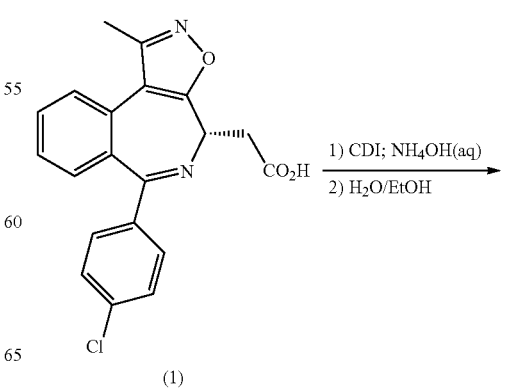

(1)

-continued

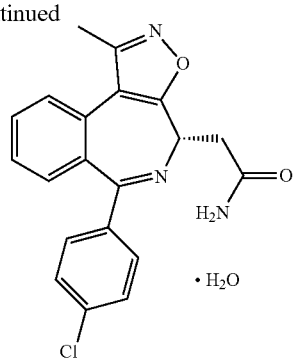

Figure 6:
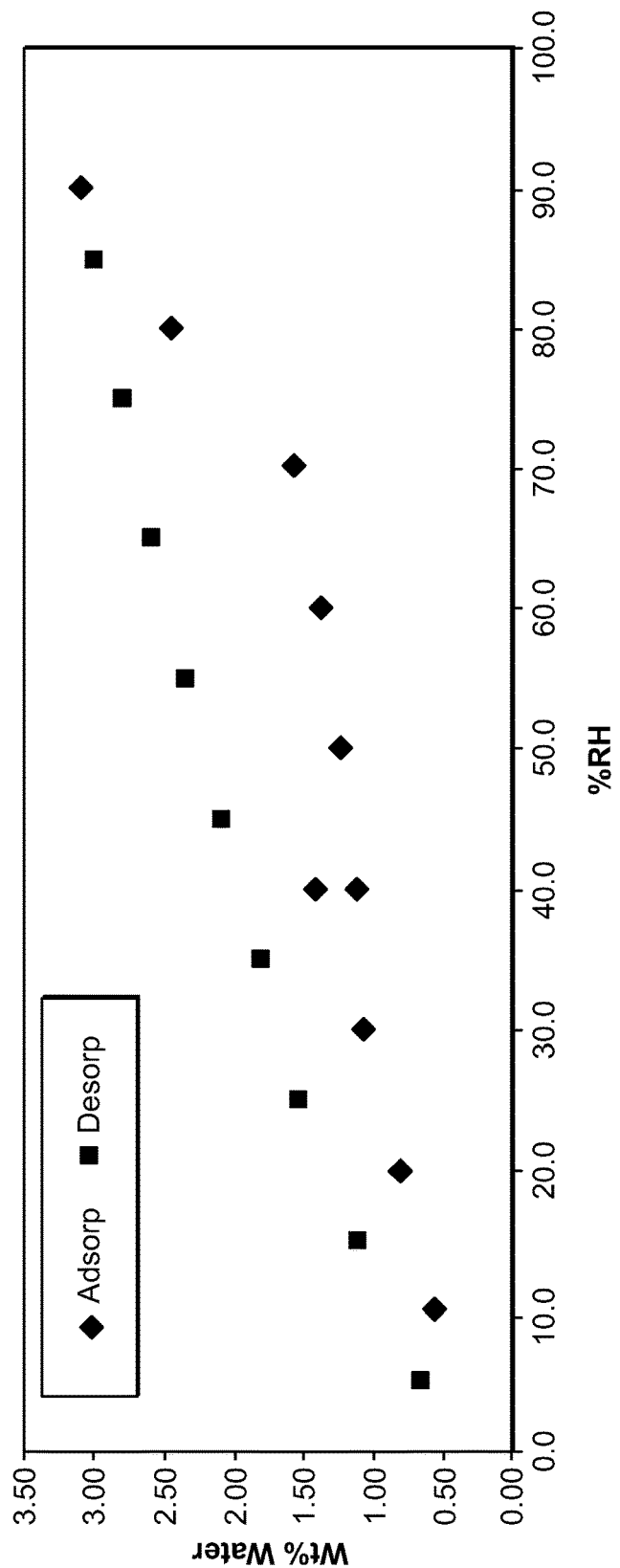
FIG. 6 depicts a gravimetric moisture sorption curve for amorphous 2-((4S)-6-(4-chlorophenyl)-1-methyl-4H-benzo[c]isoxazolo[4,5-e]azepin-4-yl)acetamide.

Carboxylic acid (1) was prepared from the procedures described in U.S. Patent Publication No. 2012/0157428. See e.g., Scheme 1, Step L of U.S. Patent Publication No. 2012/0157428. It should be noted that subsequent couplings following the procedures described in U.S. Patent Publication No. 2012/0157428 (e.g., the second step in Scheme 1, Step L) produced only amorphous 2-((4S)-6-(4-chlorophenyl)-1-methyl-4H-benzo[c]isoxazolo[4,5-e]azepin-4-yl)acetamide. This amorphous material did not result in any observable diffraction using XRPD and was further characterized e.g., by gravimetric moisture sorption (FIG. 6).

To produce crystalline material, a reactor was charged with 700 g of carboxylic acid (1) with 65.8 wt % $^1$H NMR potency (460 g, 1.3 mol) in DCM (4.6 L). The batch was charged with carbonyldiimidazole (CDI, 264 g, 1.6 mol, 1.3 equiv) in four portions with the solids addition system. Over the course of the addition, the batch temperature was 15-18° C. The batch was stirred for 1-2 hours at 20-25° C. when HPLC analysis indicated the starting material was <2%. The batch was cooled to 0-5° C. The batch was charged with 28% aqueous ammonium hydroxide solution (432 mL, 6.5 mol, 5 equiv) by an addition funnel over 20 minutes while maintaining the temperature at 0-5° C. The batch was stirred at 0-5° C. for 1 hour when HPLC analysis indicated the intermediate acyl-imidazole was <2%. The batch was warmed to 20-25° C. and DI water (2.3 L) was added. The batch was stirred vigorously for 15 minutes. The stirring was stopped and the phases were separated. The organic phase was washed with brine (2.3 L), dried (MgSO$_4$), treated with activated carbon (46 g, Darco G-60), filtered, and washed with DCM (1.5 L). The combined filtrates and washes were concentrated to dryness by rotary evaporation. The residue was redissolved in absolute alcohol (2.3 L) and heated to 50-55° C. The batch was charged with DI water (2.3 L) by addition funnel over 1 hour while maintaining the temperature 50-55° C. The batch was cooled over a period of 2 hours and an oil, instead of solids, was observed to form. The batch was reheated to 50-55° C. and gradually cooled to 15-25° C. over a period of 12-16 hours. The batch was cooled to 0-5° C. and stirred for 1-2 hours. The batch was filtered and washed with a 1:1 mixture of DI water to absolute ethanol (230 mL).

The solids were dried under high vacuum at 40-45° C. overnight to afford monohydrate crystalline Form A of 2-((4S)-6-(4-chlorophenyl)-1-methyl-4H-benzo[c]isoxazolo[4,5-e]azepin-4-yl)acetamide [320 g, 70% yield, 95.1% (AUC) by HPLC]. Robertson Microlit analyzed the palladium level to be 84 ppm. XRPD, NMR, TGA, DSC, and an optical micrograph are depicted in FIGS. 1-3 and 5. Karl Fisher analysis confirmed an average water content of 4.5 wt %. The listing of XRPD peaks shown in FIG. 1 are provided in Table 1 below.

TABLE 1

| Pos. [°2Th.] | Height [cts] | d-spacing [Å] | Rel. Int. [%] |
| --- | --- | --- | --- |
| 3.0336 | 1988.99 | 29.12462 | 52.73 |
| 3.1649 | 1327.33 | 27.91663 | 35.19 |
| 3.2884 | 1083.33 | 26.86863 | 28.72 |
| 3.4948 | 635.48 | 25.28248 | 16.85 |
| 3.9478 | 403.68 | 22.38208 | 10.70 |
| 4.0869 | 270.39 | 21.62063 | 7.17 |
| 4.7235 | 2628.10 | 18.70798 | 69.67 |
| 5.1531 | 236.70 | 17.14940 | 6.27 |
| 5.3536 | 198.61 | 16.50752 | 5.26 |
| 5.4960 | 267.67 | 16.08028 | 7.10 |
| 5.8237 | 242.60 | 15.17609 | 6.43 |
| 6.1496 | 241.07 | 14.37248 | 6.39 |
| 6.3895 | 216.18 | 13.83349 | 5.73 |
| 6.5144 | 215.41 | 13.56854 | 5.71 |
| 6.7353 | 204.99 | 13.12391 | 5.43 |
| 6.9871 | 215.41 | 12.65149 | 5.71 |
| 7.3109 | 227.93 | 12.09190 | 6.04 |
| 7.8162 | 302.06 | 11.31125 | 8.01 |
| 8.0948 | 734.50 | 10.92261 | 19.47 |
| 8.3685 | 197.39 | 10.56595 | 5.23 |
| 9.4026 | 3757.23 | 9.40614 | 99.60 |
| 9.6511 | 281.43 | 9.16446 | 7.46 |
| 9.8338 | 174.97 | 8.99467 | 4.64 |
| 11.4804 | 930.16 | 7.70797 | 24.66 |
| 12.2142 | 157.58 | 7.24649 | 4.18 |
| 12.9004 | 1039.92 | 6.86256 | 27.57 |
| 13.1776 | 982.45 | 6.71883 | 26.04 |
| 13.7115 | 667.90 | 6.45837 | 17.71 |
| 13.9053 | 1383.18 | 6.36881 | 36.67 |
| 14.0985 | 3561.75 | 6.28194 | 94.42 |
| 14.4812 | 248.41 | 6.11678 | 6.59 |
| 14.9529 | 432.73 | 5.92489 | 11.47 |
| 15.2740 | 230.77 | 5.80102 | 6.12 |
| 15.5561 | 531.22 | 5.69646 | 14.08 |
| 16.1928 | 268.83 | 5.47389 | 7.13 |
| 16.6155 | 277.70 | 5.33556 | 7.36 |
| 17.6687 | 283.77 | 5.01985 | 7.52 |
| 18.0818 | 1412.20 | 4.90606 | 37.44 |
| 18.4628 | 1032.14 | 4.80568 | 27.36 |
| 18.8178 | 3772.24 | 4.71581 | 100.00 |
| 19.2547 | 235.31 | 4.60979 | 6.24 |
| 19.6750 | 1469.98 | 4.51226 | 38.97 |
| 19.9576 | 201.73 | 4.44899 | 5.35 |
| 20.1690 | 316.47 | 4.40283 | 8.39 |
| 20.4059 | 638.01 | 4.35224 | 16.91 |
| 21.1124 | 291.75 | 4.20818 | 7.73 |
| 21.4065 | 1204.64 | 4.15103 | 31.93 |
| 21.9339 | 862.26 | 4.05239 | 22.86 |
| 22.2025 | 1399.21 | 4.00397 | 37.09 |
| 22.7872 | 436.98 | 3.90253 | 11.58 |
| 23.0528 | 893.69 | 3.85817 | 23.69 |
| 23.3225 | 749.60 | 3.81417 | 19.87 |
| 23.6892 | 412.87 | 3.75595 | 10.94 |
| 24.2339 | 1031.93 | 3.67274 | 27.36 |
| 25.1459 | 1568.45 | 3.54156 | 41.58 |
| 26.0516 | 1213.60 | 3.42046 | 32.17 |
| 26.4951 | 606.60 | 3.36420 | 16.08 |
| 26.8154 | 558.47 | 3.32474 | 14.80 |
| 27.3459 | 360.81 | 3.26144 | 9.56 |
| 27.8110 | 411.96 | 3.20795 | 10.92 |
| 28.5558 | 302.69 | 3.12594 | 8.02 |
| 28.7720 | 149.82 | 3.10294 | 3.97 |
| 29.0442 | 406.42 | 3.07448 | 10.77 |
| 30.0560 | 307.13 | 2.97325 | 8.14 |
| 30.9196 | 206.76 | 2.89215 | 5.48 |
| 31.6090 | 444.00 | 2.83063 | 11.77 |
| 32.2544 | 62.89 | 2.77544 | 1.67 |
| 32.8271 | 163.83 | 2.72832 | 4.34 |
| 33.1645 | 177.25 | 2.70133 | 4.70 |
| 33.7924 | 382.04 | 2.65256 | 10.13 |
| 34.6255 | 229.21 | 2.59062 | 6.08 |
| 36.2737 | 143.43 | 2.47660 | 3.80 |
| 36.9392 | 48.33 | 2.43350 | 1.28 |
| 37.4803 | 54.57 | 2.39960 | 1.45 |
| 38.1235 | 94.49 | 2.36058 | 2.50 |
| 38.6912 | 84.88 | 2.32725 | 2.25 |
| 39.6424 | 51.55 | 2.27357 | 1.37 |
| 40.1581 | 73.63 | 2.24556 | 1.95 |

TABLE 1-continued

| Pos. [°2Th.] | Height [cts] | d-spacing [A] | Rel. Int. [%] |
|---|---|---|---|
| 41.1015 | 59.40 | 2.19617 | 1.57 |
| 42.0541 | 24.56 | 2.14860 | 0.65 |
| 43.0617 | 132.72 | 2.10063 | 3.52 |
| 44.4472 | 57.70 | 2.03663 | 1.53 |

Figure 11:
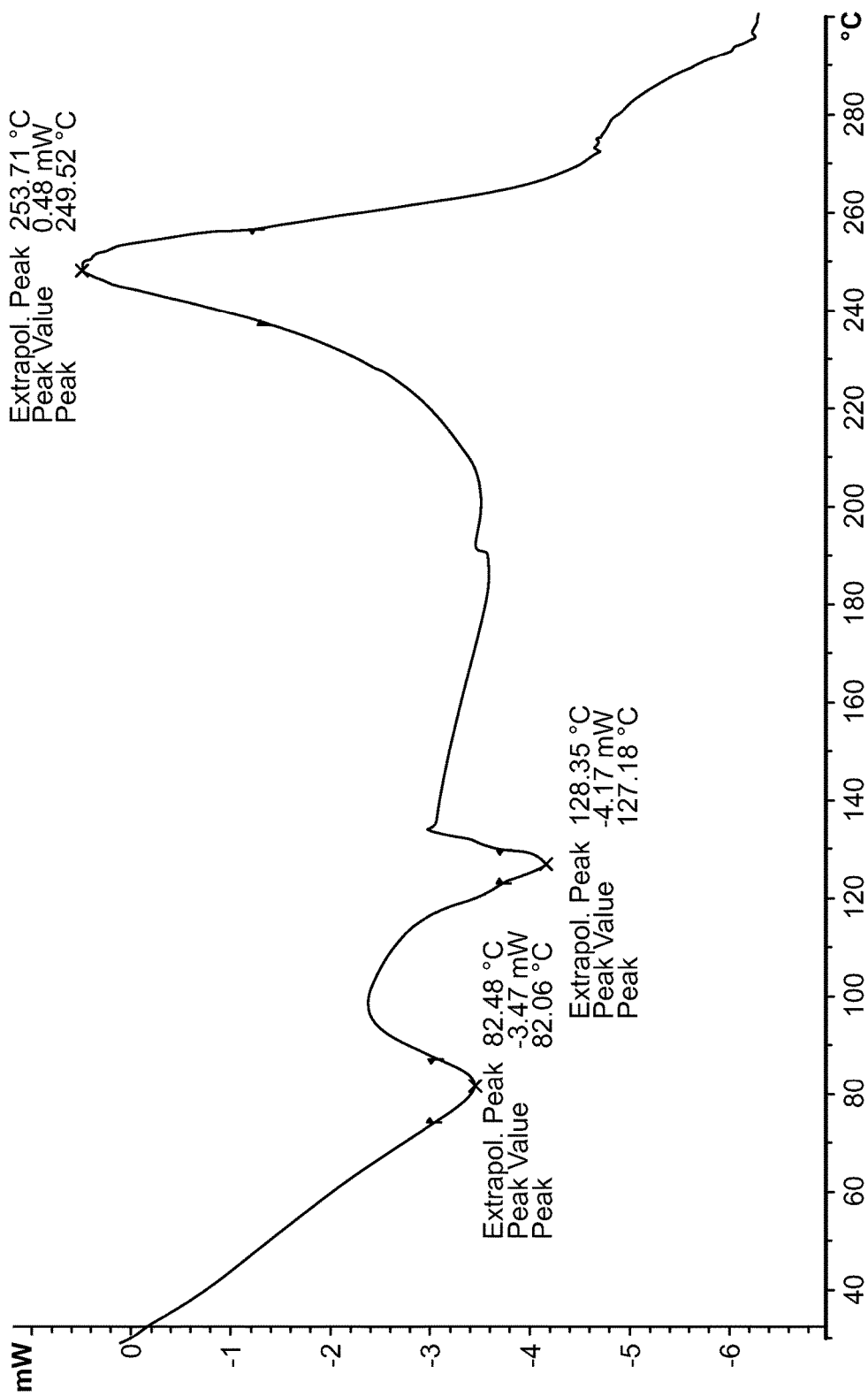
FIG. 11 depicts a Differential Scanning calorimetry (DSC) spectrum for GMP scale up of monohydrate crystalline Form A of 2-((4S)-6-(4-chlorophenyl)-1-methyl-4H-benzo[c]isoxazolo[4,5-e]azepin-4-yl)acetamide.
Figure 12:
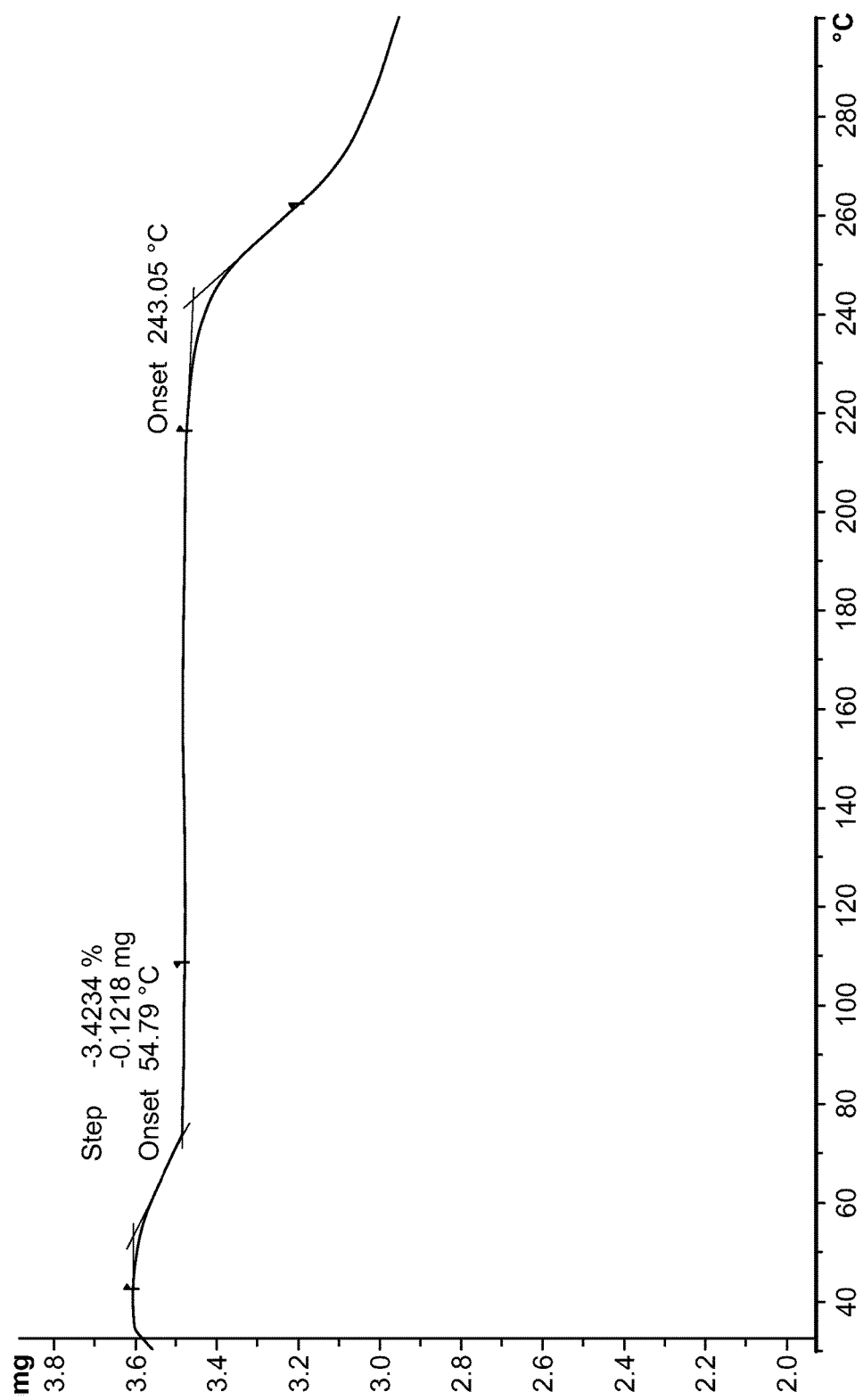
FIG. 12 depicts a thermal gravimetric analysis (TGA) pattern for GMP scale up of monohydrate crystalline Form A of 2-((4S)-6-(4-chlorophenyl)-1-methyl-4H-benzo[c]isoxazolo[4,5-e]azepin-4-yl)acetamide.

GMP scale up of monohydrate crystalline Form A was performed as follows. 3955 g of crude 2-((4S)-6-(4-chlorophenyl)-1-methyl-4H-benzo[c]isoxazolo[4,5-e]azepin-4-yl)acetamide, was dissolved in prefiltered EtOH (15 L, 5.5 vol) at room temperature and transferred to a 100 L, jacketed reactor. The batch temperature was set to 55±5° C. and purified water (15 L, 5.5 vol) was added while maintaining the batch temperature at 55±5° C. over a period of 42 min. Batch temperature was set to 45±5° C. and monohydrate Form A Seed Crystals (6.1 g) were added. The batch was cooled to 20±5° C. over a period of 5 h and further cooled to 0±5° C. over a period of 55 min. Stirring continued for an additional 1 h at 0±5° C. The resulting solids were filtered and the filter cake was washed with a 1:1 room temperature mixture of prefiltered ethanol (1.5 L) and purified water (1.5 L). The solids were transferred to glass trays and dried in a vacuum oven at 45±5° C. with a nitrogen bleed to provide 2.15 kg (75%) of monohydrate crystalline Form A as an off-white solid. XRPD, DSC, and TGA are depicted in FIGS. 10-12. Karl Fisher analysis confirmed a water content of 4.3 wt %. The listing of XRPD peaks shown in FIG. 10 are provided in Table 2 below.

TABLE 2

| Pos. [°2Th.] | Height [cts] | d-spacing [A] | Rel. Int. [%] |
|---|---|---|---|
| 3.4080 | 740.11 | 25.92592 | 54.27 |
| 3.8112 | 343.38 | 23.18414 | 25.18 |
| 3.9533 | 413.37 | 22.35104 | 30.31 |
| 4.2321 | 235.42 | 20.87945 | 17.26 |
| 4.4246 | 449.77 | 19.97141 | 32.98 |
| 4.7265 | 1019.48 | 18.69635 | 74.76 |
| 5.4063 | 238.73 | 16.34693 | 17.51 |
| 5.7155 | 226.66 | 15.46312 | 16.62 |
| 6.0881 | 196.79 | 14.51766 | 14.43 |
| 6.5332 | 166.88 | 13.52957 | 12.24 |
| 7.0002 | 254.60 | 12.62787 | 18.67 |
| 7.2643 | 188.77 | 12.16931 | 13.84 |
| 7.6543 | 183.76 | 11.55018 | 13.47 |
| 8.1056 | 527.23 | 10.90808 | 38.66 |
| 9.0552 | 260.59 | 9.76617 | 19.11 |
| 9.4205 | 1036.06 | 9.38832 | 75.97 |
| 10.2693 | 190.66 | 8.61415 | 13.98 |
| 10.7274 | 115.42 | 8.24730 | 8.46 |
| 10.9628 | 145.29 | 8.07073 | 10.65 |
| 11.4960 | 574.76 | 7.69754 | 42.15 |
| 11.9277 | 131.43 | 7.41995 | 9.64 |
| 12.2366 | 234.28 | 7.23329 | 17.18 |
| 12.9118 | 978.84 | 6.85650 | 71.78 |
| 13.1919 | 1003.96 | 6.71154 | 73.62 |
| 13.6997 | 640.80 | 6.46391 | 46.99 |
| 13.9273 | 1276.77 | 6.35878 | 93.62 |
| 14.0969 | 1264.85 | 6.28265 | 92.75 |
| 14.5209 | 235.92 | 6.10015 | 17.30 |
| 14.9684 | 476.37 | 5.91879 | 34.93 |
| 15.5806 | 246.37 | 5.68756 | 18.07 |
| 16.2278 | 218.55 | 5.46216 | 16.03 |
| 16.6266 | 195.39 | 5.33205 | 14.33 |
| 17.3982 | 123.37 | 5.09725 | 9.05 |
| 17.6658 | 302.19 | 5.02064 | 22.16 |
| 18.0877 | 1305.56 | 4.90447 | 95.73 |
| 18.4827 | 882.00 | 4.80054 | 64.67 |
| 18.7987 | 1285.08 | 4.72056 | 94.23 |
| 19.2100 | 257.04 | 4.62041 | 18.85 |
| 19.7033 | 1073.72 | 4.50582 | 78.73 |

TABLE 2-continued

| Pos. [°2Th.] | Height [cts] | d-spacing [A] | Rel. Int. [%] |
|---|---|---|---|
| 20.2147 | 321.21 | 4.39299 | 23.55 |
| 20.4209 | 380.63 | 4.34909 | 27.91 |
| 21.1031 | 150.77 | 4.21001 | 11.06 |
| 21.4152 | 941.01 | 4.14935 | 69.00 |
| 21.9650 | 602.58 | 4.04671 | 44.18 |
| 22.1686 | 562.27 | 4.01001 | 41.23 |
| 22.8147 | 320.56 | 3.89789 | 23.51 |
| 23.0759 | 644.48 | 3.85436 | 47.26 |
| 23.3517 | 549.90 | 3.80946 | 40.32 |
| 23.7273 | 277.30 | 3.75000 | 20.33 |
| 24.2598 | 1100.96 | 3.66887 | 80.73 |
| 25.1699 | 1363.76 | 3.53825 | 100.00 |
| 26.0748 | 810.12 | 3.41747 | 59.40 |
| 26.5288 | 465.03 | 3.36001 | 34.10 |
| 26.8295 | 329.14 | 3.32303 | 24.13 |
| 27.3416 | 308.65 | 3.26194 | 22.63 |
| 27.8286 | 280.09 | 3.20595 | 20.54 |
| 28.5953 | 220.56 | 3.12172 | 16.17 |
| 28.8334 | 196.35 | 3.09648 | 14.40 |
| 29.0462 | 278.36 | 3.07173 | 20.41 |
| 29.1504 | 283.60 | 3.06352 | 20.80 |
| 30.0960 | 306.43 | 2.96939 | 22.47 |
| 30.9361 | 102.55 | 2.89064 | 7.52 |
| 31.5911 | 306.56 | 2.83219 | 22.48 |
| 32.8056 | 115.64 | 2.73006 | 8.48 |
| 33.1879 | 97.15 | 2.69948 | 7.12 |
| 33.7004 | 221.32 | 2.65959 | 16.23 |
| 34.6463 | 144.49 | 2.58912 | 10.60 |
| 35.6301 | 23.03 | 2.51985 | 1.69 |
| 36.2831 | 67.12 | 2.47598 | 4.92 |
| 36.8903 | 50.77 | 2.43661 | 3.72 |
| 37.4872 | 45.00 | 2.39918 | 3.30 |
| 39.7062 | 48.73 | 2.27007 | 3.57 |
| 40.0574 | 39.85 | 2.25097 | 2.92 |
| 40.8783 | 44.10 | 2.20764 | 3.23 |
| 41.2199 | 21.83 | 2.19014 | 1.60 |
| 43.0651 | 70.94 | 2.10047 | 5.20 |
| 44.4896 | 35.20 | 20.3479 | 2.58 |

Examples of formulations comprising the crystalline forms described herein are as follows.

2 mg Capsules

| Ingredients | Function | Weight Composition (%, w/w) | Weight per Unit Dosage (mg) |
|---|---|---|---|
| Monohydrate Cystalline Form A | API | 1.25 | 2.0 |
| Microcrystalline Cellulose (Avicel PH-101) | Filler | 97.75 | 156.4 |
| Magnesium Stearate (Vegetable Grade, Hyqual) | Lubricant | 1.00 | 1.6 |
| HPMC capsule, size 2, white opaque (Vcaps Plus) | Capsule shell | NA | 1 each |
| Total | | 100.00 | 160.0 |

10 mg Capsules

| Ingredients | Function | Weight Composition (%, w/w) | Weight per Unit Dosage (mg) |
|---|---|---|---|
| Monohydrate Cystalline Form A | API | 3.60 | 10.0 |
| Microcrystalline Cellulose (Avicel PH-101) | Filler | 95.00 | 267.2 |
| Magnesium Stearate (Vegetable Grade, Hyqual) | Lubricant | 1.00 | 2.8 |
| HPMC capsule, size 0, Swedish Orange (Quali Vcaps) | Capsule shell | NA | 1 each |
| Total | | 100.00 | 280.0 |

25 mg Capsules

| Ingredients | Function | Weight Composition (%, w/w) | Weight per Unit Dosage (mg) |
|---|---|---|---|
| Monohydrate Cystalline Form A | API | 8.93 | 25.0 |
| Microcrystalline Cellulose (Avicel PH-101) | Filler | 90.57 | 253.6 |
| Magnesium Stearate (Vegetable Grade, Hyqual) | Lubricant | 0.50 | 1.4 |
| HPMC capsule, size 0, Rich yellow Opaque (Vcap Plus) | Capsule shell | NA | 1 each |
| Total | | 100.00 | 280.0 |

Micronized Forms

| Ingredient | Function | weight composition (w/w %) | weight (mg) per unit dosage (25 mg tablet) | weight (mg) per unit dosage (50 mg tablet) | weight (mg) per unit dosage (100 mg tablet) |
|---|---|---|---|---|---|
| Intragranular | | | | | |
| Micronized Monohydrate Form A | API | 12.5 | 25.0 | 50.0 | 100.0 |
| Microcrystalline cellulose | Diluent/filler | 30.0 | 60.0 | 120.0 | 240.0 |
| Lactose monohydrate | Diluent/filler | 45.0 | 90.0 | 180.0 | 360.0 |
| Croscarmellose sodium | Disintegrant | 2.0 | 4.0 | 8.0 | 16.0 |
| Hydroxypropyl cellulose | Binder | 3.5 | 7.0 | 14.0 | 28.0 |
| Sodium lauryl sulfate | surfactant | 3.0 | 6.0 | 12.0 | 24.0 |
| Purified water | Granulating liquid | qs | qs | qs | qs |
| Extragranular | | | | | |
| Croscarmellose sodium | Disintegrant | 2.0 | 4.0 | 8.0 | 16.0 |
| Colloidal silicon dioxide | Glidant | 1.0 | 2.0 | 4.0 | 8.0 |
| Magnesium stearate | Lubricant | 1.0 | 2.0 | 4.0 | 8.0 |
| Total intragranular | | 100.0 | 200.0 | 400.0 | 800.0 |

Figure 4:
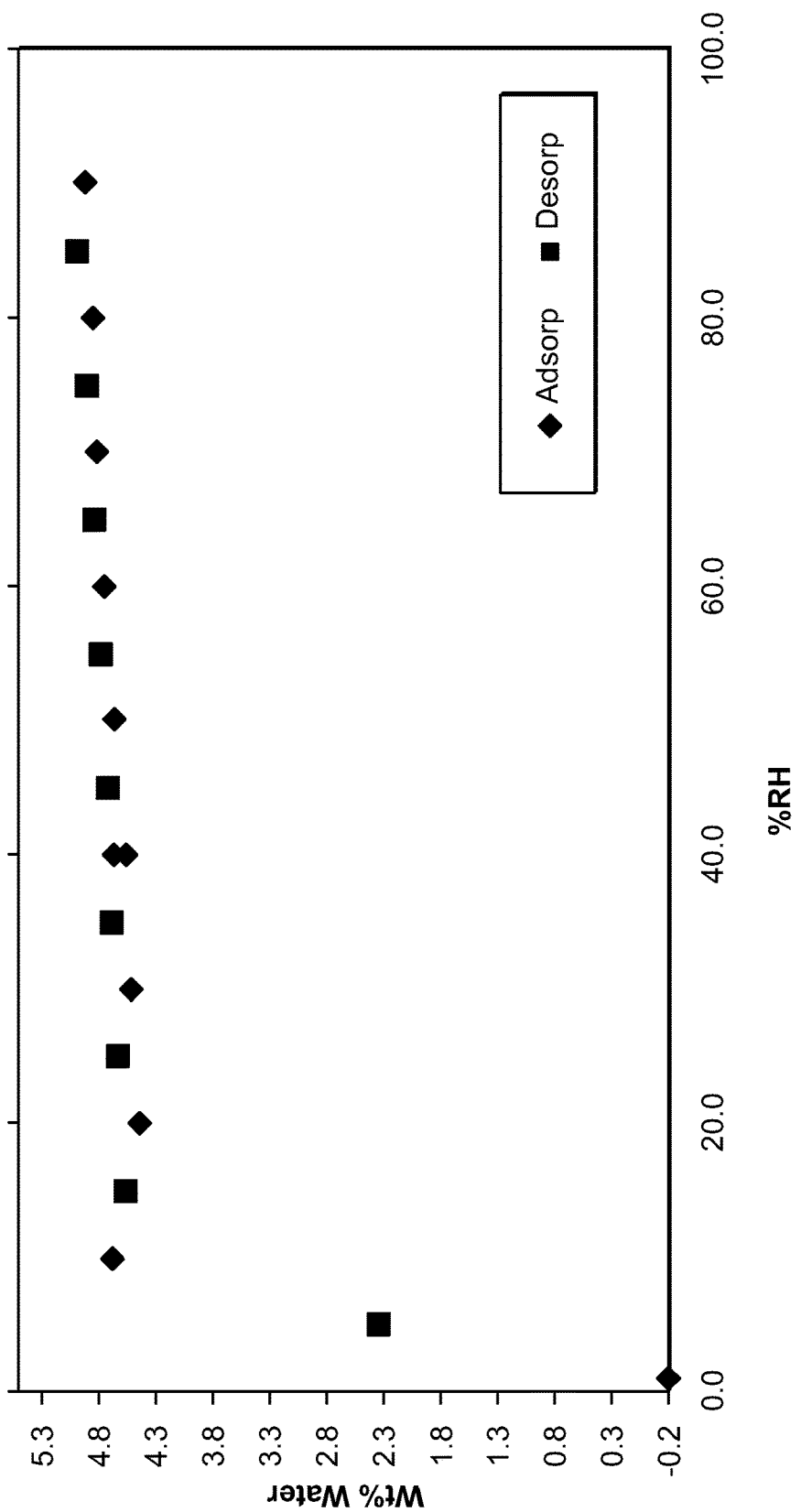
FIG. 4 depicts a gravimetric moisture sorption curve for monohydrate crystalline Form A of 2-((4S)-6-(4-chlorophenyl)-1-methyl-4H-benzo[c]isoxazolo[4,5-e]azepin-4-yl)acetamide.

Certain Advantages of Monohydrate Form A Over Amorphous 2-((4S)-6-(4-chlorophenyl)-1-methyl-4H-benzo[c]isoxazolo[4,5-e]azepin-4-yl)acetamide Relative Humidity Stability As shown by the gravimetric moisture sorption curve for monohydrate Form A of 2-((4S)-6-(4-chlorophenyl)-1-methyl-4H-benzo[c]isoxazolo[4,5-e]azepin-4-yl)acetamide in FIG. 4, the stability of the monohydrate stoichiometry (water content) remains effectively constant at the monohydrate state (at approximately 5%, theoretical content of 4.6%) over a relative humidity range of 5 to 95%. This level of stability is rare for many pharmaceutical compounds, and particularly for hydrated forms since most are typically stable only at lower threshold values. Typically, one would expect to see stability of a monohydrate stoichiometry over a more limited range, e.g., between 30 to 70%. At relative humidity levels below 30% a compound would still retain water, but the stoichiometric ratio would be less than that of a true monohydrate. Likewise, at high relative humidity, the stoichiometric ratio of water to compound would exceed that of a monohydrate. As evidenced by FIG. 4, this was not observed with monohydrate Form A of 2-((4S)-6-(4-chlorophenyl)-1-methyl-4H-benzo[c]isoxazolo[4,5-e]azepin-4-yl)acetamide. Rather, the stoichiometric ratio of water to monohydrate remained stable throughout the relative humidity range of 5 to 95%.

This unanticipated observed stability of the monohydrate Form A over such a broad humidity range would be advantageous in pharmaceutical formulations (e.g., tablets and capsules) since the water content of monohydrate Form A should have minimal effect on the water content of excipients and, likewise, the water content of the excipients would have minimal impact on the monohydrate Form A water content.

Unlike the moisture vapor profile of the disclosed monohydrate Form A, the water content of microcrystalline cellulose changes from 4 wt % at 20% relative humidity to approximately 18 wt % at 90% relative humidity. In a pharmaceutical formulation blend comprising an API with an excipient like, e.g., microcrystalline cellulose, or in a compressed tablet, the water content of the API and the excipients will equilibrate. Since the water content of the disclosed monohydrate Form A remains very consistent from 5 to 95% RH one achieves the unexpected advantage of not having to be concerned with the excipient(s) (e.g., microcrystalline cellulose) giving up water to the API or vice versa, which could lead to changes in API stability or to changes in friabitly or disintegration properties upon storage.

In contrast, FIG. 6 shows a gravimetric moisture sorption curve for amorphous 2-((4S)-6-(4-chlorophenyl)-1-methyl-4H-benzo[c]isoxazolo[4,5-e]azepin-4-yl)acetamide, where the water content of the amorphous form was found to increase from 0 to approximately 95% relative humidity. Thus, and in contrast to the disclosed monohydrate Form A, amorphous 2-((4S)-6-(4-chlorophenyl)-1-methyl-4H-benzo[c]isoxazolo[4,5-e]azepin-4-yl)acetamide does not exhibit an effectively constant stoichiometric ratios of water over a broad relative humidity range and, as such, the aforementioned concerns and changes may be realized.

Relative Stability

In deionized water, the monohydrate Form A was found to be stable with a solubility of 4.5 μm/mL. However, upon slurry of the amorphous form in deionized water for 24 hr at ambient temperature conversion to monohydrate Form A was observed.

Pharmacokinetic Comparison of Monohydrate Form A and Amorphous 2-((4S)-6-(4-chlorophenyl)-1-methyl-4H-benzo[c]isoxazolo[4,5-e]azepin-4-yl)acetamide For many active pharmaceutical ingredients it has been shown that different forms have different pharmacokinetic profiles. Compared to amorphous solid, crystalline solids have often lower oral bioavailability (Qiu Y., J Pharm Sci, 2004, 93:563). Data below demonstrates that monohydrate Form A of 2-((4S)-6-(4-chlorophenyl)-1-methyl-4H-benzo[c]isoxazolo[4,5-e]azepin-4-yl)acetamide has favorable pharmacokinetic profile in rats and dogs and are similar to what was observed with the amorphous solid. Results demonstrate that Form A is suitable for use in human for treatment of disease.

Monohydrate Form A of 2-((4S)-6-(4-chlorophenyl)-1-methyl-4H-benzo[c]isoxazolo[4,5-e]azepin-4-yl)acetamide was discovered to have the following favorable and unexpected properties: similar pharmacokinetic profile to the amorphous solid when administered as a suspension in Methylcellulose; small inter-individual variability; acceptable dose exposure proportionality; and favorable pharmacokinetic profile when administered as powder in a capsule.

Pharmacokinetic of Monohydrate Form A and Amorphous 2-((4S)-6-(4-chlorophenyl)-1-methyl-4H-benzo[c]isoxazolo[4,5-e]azepin-4-yl)acetamide in Rat Male Sprague Dawley rats were dosed at 60 mg/Kg orally once using a suspension of amorphous 2-((4S)-6-(4-chlorophenyl)-1-methyl-4H-benzo[c]isoxazolo[4,5-e]azepin-4-yl)acetamide in 0.5% Methylcellulose. Individual plasma concentrations are reported in Table 3 and calculated pharmacokinetic parameters are reported in Table 4.

TABLE 3

Plasma concentration of amorphous 2-((4S)-6-(4-chlorophenyl)-1-methyl-4H-benzo[c]isoxazolo[4,5-e]azepin-4-yl)acetamide following single oral dose to male Sprague Dawley rats at 60 mg/Kg.

| Time (h) | R 2007 | R 2008 | R 2009 | R 2010 | R 2011 | R 2012 | Mean |
|---|---|---|---|---|---|---|---|
| 1 | | | | 12700 | 13800 | 8650 | 11700 |
| 2 | 14900 | 12100 | 8830 | | | | 11900 |
| 4 | | | | 8410 | 11800 | 9370 | 9860 |
| 8 | 6550 | 6450 | 6310 | | | | 6440 |
| 24 | | | | BQL | BQL | BQL | BQL |

TABLE 4

Calculated pharmacokinetic parameters of amorphous 2-((4S)-6-(4-chlorophenyl)-1-methyl-4H-benzo[c]isoxazolo[4,5-e]azepin-4-yl)acetamide following single oral dose to male Sprague Dawley rats at 60 mg/Kg.

| | |
|---|---|
| $C_{max}$ (ng/mL) | 11900 |
| $T_{max}$ (h) | 2.0 |
| $AUC_{0-last}$ (ng · h/mL) | 123000 |

Male Sprague Dawley rats were dosed at 60 mg/Kg orally once using a suspension of monohydrate Form A of 2-((4S)-6-(4-chlorophenyl)-1-methyl-4H-benzo[c]isoxazolo[4,5-e]azepin-4-yl)acetamide in 0.5% Methylcellulose. Individual plasma concentrations are reported in Table 5 and calculated pharmacokinetic parameters are reported in Table 6.

TABLE 5

Plasma concentration of monohydrate Form A of 2-((4S)-6-(4-chlorophenyl)-1-methyl-4H-benzo[c]isoxazolo[4,5-e]azepin-4-yl)acetamide following single oral dose to male Sprague Dawley rats at 60 mg/Kg.

| Time (h) | R7 | R8 | R9 | R10 | R11 | R12 | Mean | | SD |
|---|---|---|---|---|---|---|---|---|---|
| 0.0830 | 183 | 407 | 512 | 158 | 391 | 172 | 304 | ± | 152 |
| 0.250 | 1830 | 2770 | 2670 | 2150 | 2050 | 1420 | 2148 | ± | 510 |
| 0.500 | 3610 | 5250 | 3790 | 4120 | 4050 | 3550 | 4062 | ± | 625 |
| 1.00 | 5290 | 6110 | 6840 | 5440 | 4740 | 4770 | 5532 | ± | 815 |
| 2.00 | 8220 | 7490 | 6700 | 8330 | 6850 | 5590 | 7197 | ± | 1036 |
| 4.00 | 7740 | 4850 | 5160 | 8350 | 5690 | 4650 | 6073 | ± | 1579 |
| 8.00 | 3050 | 805 | 1220 | 1960 | 2320 | 1200 | 1759 | ± | 841 |
| 24.0 | BQL | BQL | BQL | 1.04 | BQL | BQL | ND | ± | — |

TABLE 6

Calculated pharmacokinetic parameters of monohydrate Form A of 2-((4S)-6-(4-chlorophenyl)-1-methyl-4H-benzo[c]isoxazolo[4,5-e]azepin-4-yl)acetamide following single oral dose to male Sprague Dawley rats at 60 mg/Kg.

| | |
|---|---|
| $C_{max}$ (ng/mL) | 7197 |
| $T_{max}$ (h) | 2.0 |
| $AUC_{0-last}$ (ng · h/mL) | 52800 |

Based on those two studies in male Sprague Dawley rats at 60 mg/Kg, monohydrate Form A of 2-((4S)-6-(4-chlorophenyl)-1-methyl-4H-benzo[c]isoxazolo[4,5-e]azepin-4-yl)acetamide has a similar pharmacokinetic profile to the amorphous form when administered as a suspension in Methylcellulose. This is a favorable and unexpected property of the monohydrate crystalline form.

Dose Escalation with Form A in Male Sprague Dawley Rats

Figure 7:
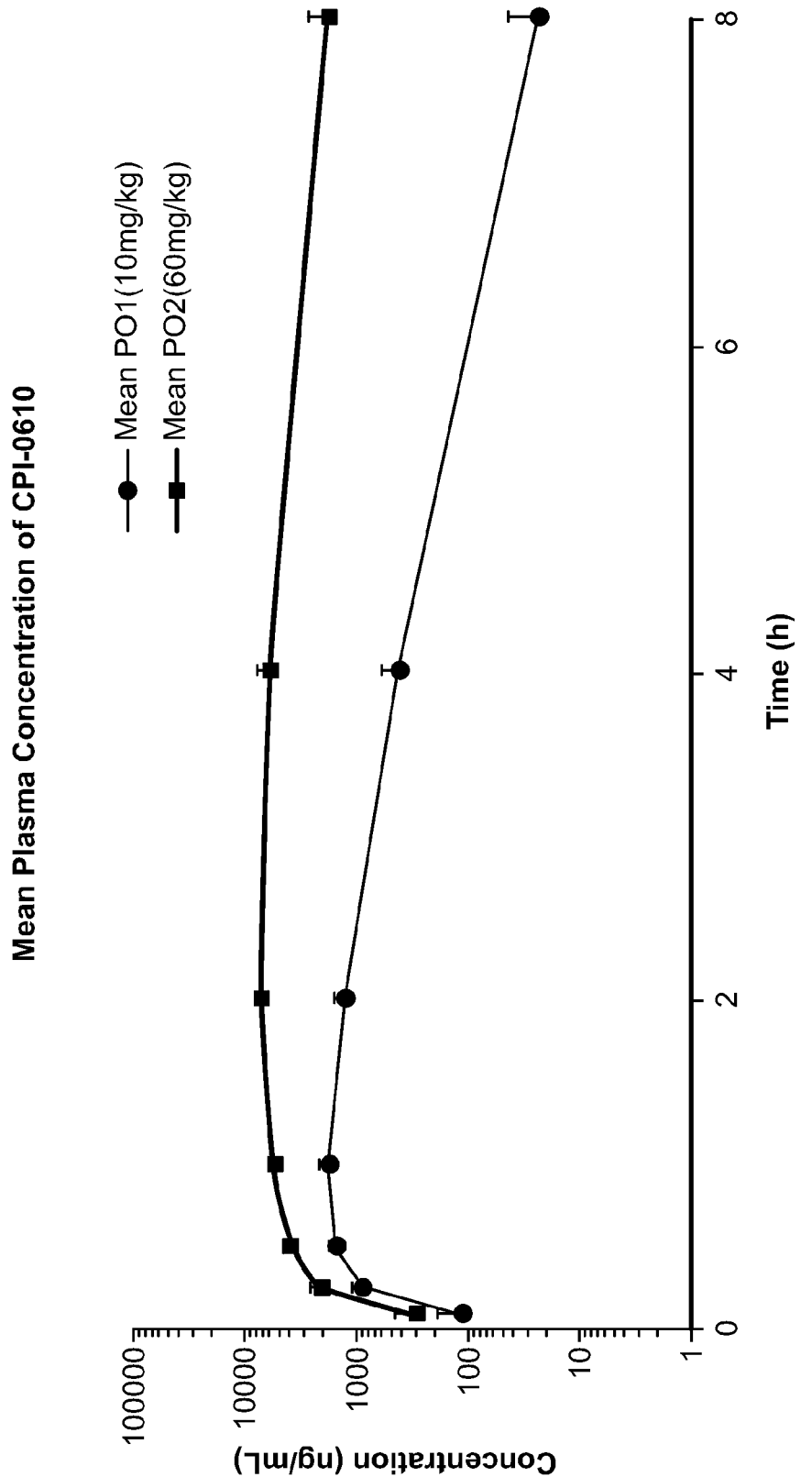
FIG. 7 depicts Individual Plasma Concentration vs. time in male Sprague Dawley rats after oral administration with monohydrate crystalline Form A of 2-((4S)-6-(4-chlorophenyl)-1-methyl-4H-benzo[c]isoxazolo[4,5-e]azepin-4-yl)acetamide in 0.5% MC at 10 and 60 mg/kg.
Figure 8:
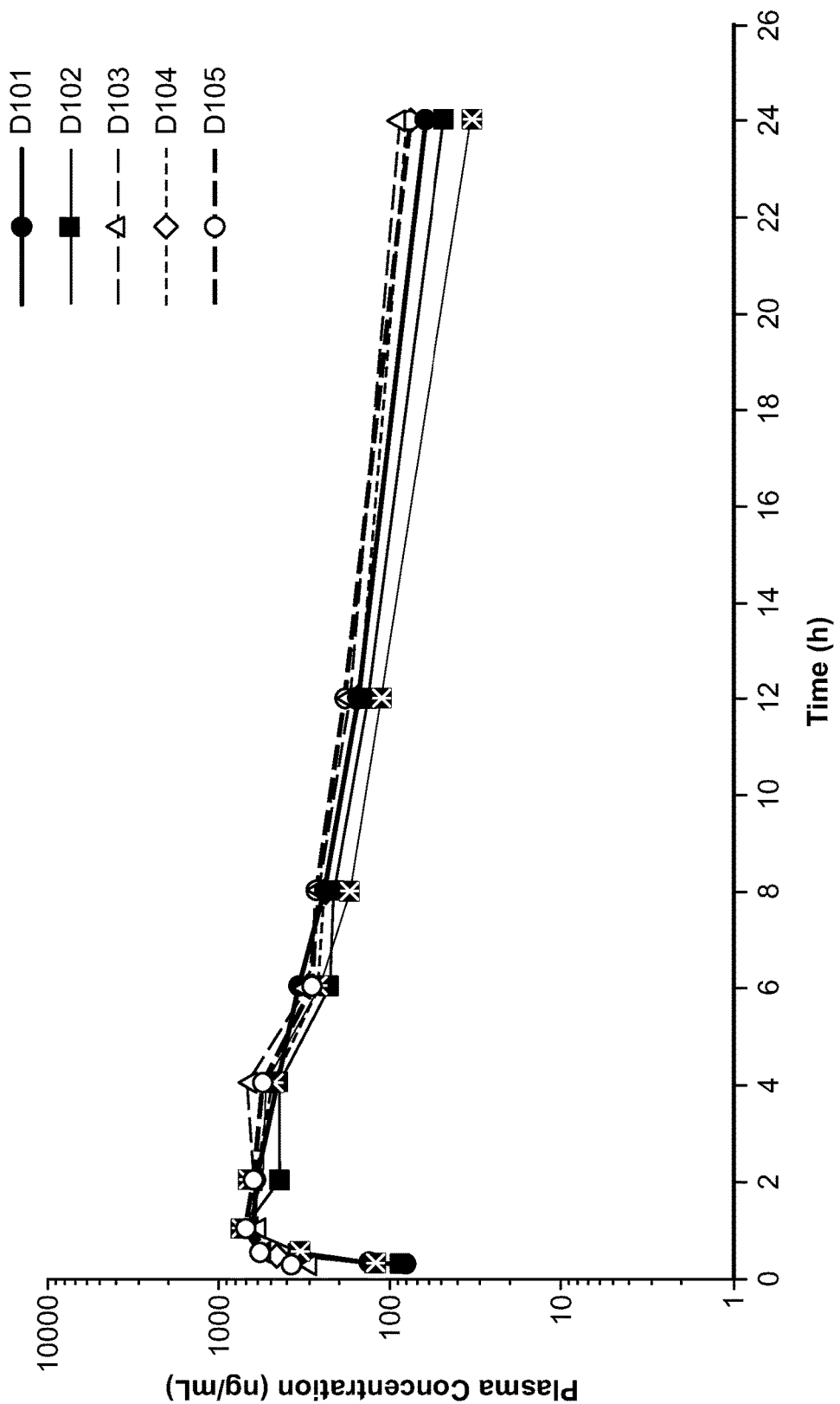
FIG. 8 depicts Individual Plasma Concentration vs. time in Male Beagle Dogs after Oral Administration with amorphous 2-((4S)-6-(4-chlorophenyl)-1-methyl-4H-benzo[c]isoxazolo[4,5-e]azepin-4-yl)acetamide in 0.5% MC at 2 mg/kg.
Figure 9:
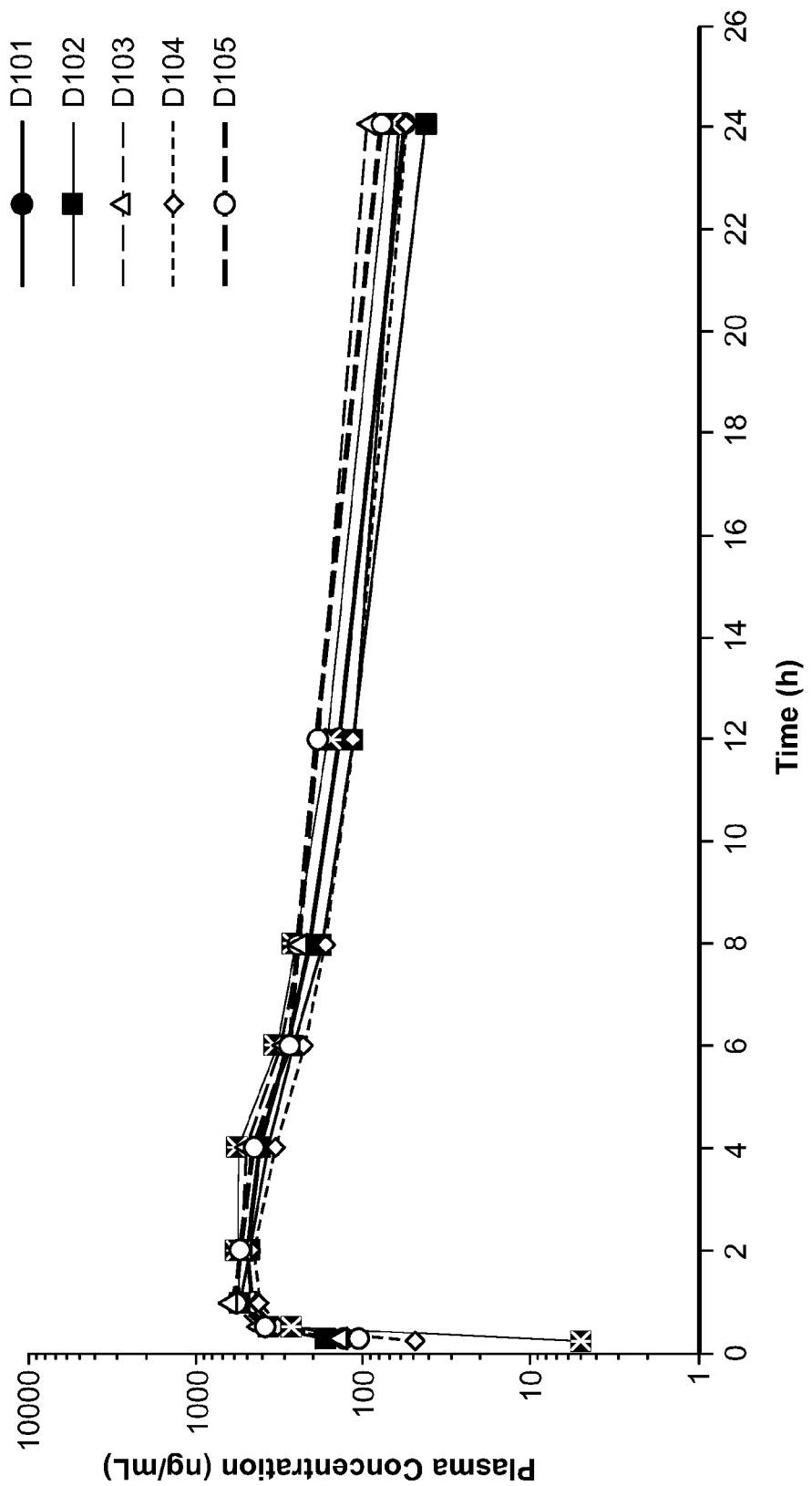
FIG. 9 depicts Individual Plasma Concentration vs. time in Male Beagle Dogs after Oral Administration with monohydrate crystalline Form A of 2-((4S)-6-(4-chlorophenyl)-1-methyl-4H-benzo[c]isoxazolo[4,5-e]azepin-4-yl)acetamide in 0.5% MC at 2 mg/kg.

A suspension of monohydrate Form A of 2-((4S)-6-(4-chlorophenyl)-1-methyl-4H-benzo[c]isoxazolo[4,5-e]azepin-4-yl)acetamide suspended in 0.5% Methylcellulose was dosed to Male Sprague Dawley rats at 10 mg/Kg and 60 mg/Kg orally. Individual plasma concentrations for the 10 mg/Kg dose and the 60 mg/Kg dose are reported on Table 7 and Table 5 respectively. Respective pharmacokinetic parameters and pharmacokinetic profiles are reported in Table 8 and in FIG. 7.

TABLE 7

Plasma concentration of monohydrate Form A of 2-((4S)-6-(4-chlorophenyl)-1-methyl-4H-benzo[c]isoxazolo[4,5-e]azepin-4-yl)acetamide following single oral dose to male Sprague Dawley rats at 10 mg/Kg.

| Time (h) | R1 | R2 | R3 | R4 | R5 | R6 | PO1 | | SD |
|---|---|---|---|---|---|---|---|---|---|
| 0.0830 | 51.3 | 182 | 89.2 | 191 | 166 | 31.5 | 119 | ± | 70.0 |
| 0.250 | 799 | 1240 | 809 | 1060 | 767 | 769 | 907 | ± | 197 |
| 0.500 | 1420 | 1410 | 1420 | 2000 | 1440 | 1600 | 1548 | ± | 233 |
| 1.00 | 1940 | 1620 | 1510 | 2300 | 1790 | 1600 | 1793 | ± | 292 |
| 2.00 | 1400 | 1320 | 1420 | 1650 | 950 | 1000 | 1290 | ± | 268 |
| 4.00 | 611 | 349 | 569 | 544 | 166 | 255 | 416 | ± | 185 |
| 8.00 | 56.3 | 18.1 | 32.4 | 13.6 | 2.93 | 18.2 | 23.6 | ± | 18.6 |
| 24.0 | BQL | BQL | BQL | BQL | BQL | BQL | ND | ± | — |

TABLE 8

Calculated pharmacokinetic parameters of monohydrate Form A of 2-((4S)-6-(4-chlorophenyl)-1-methyl-4H-benzo[c]isoxazolo[4,5-e]azepin-4-yl)acetamide following single oral dose to male Sprague Dawley rats at 10 and 60 mg/Kg.

| Doses (mg/Kg) | 10 | 60 |
|---|---|---|
| $C_{max}$ (ng/mL) | 1793 | 7197 |
| $T_{max}$ (h) | 1.0 | 2.0 |
| $AUC_{0-last}$ (ng · h/mL) | 5500 | 52800 |

When monohydrate Form A of 2-((4S)-6-(4-chlorophenyl)-1-methyl-4H-benzo[c]isoxazolo[4,5-e]azepin-4-yl)acetamide is administered orally as a suspension in Methylcellulose in male Sprague Dawley rats, both the Cmax and the AUC increase slightly more than proportionally with the dose as the dose increases from 10 to 60 mg/Kg. (See e.g., FIG. 7). Low inter-individual differences are also observed at both doses. These are favorable and unexpected properties of the monohydrate crystalline Form A solid.

Pharmacokinetic of Monohydrate Form A and Amorphous 2-((4S)-6-(4-chlorophenyl)-1-methyl-4H-benzo[c]isoxazolo[4,5-e]azepin-4-yl)acetamide in Dog Amorphous and monohydrate Form A of 2-((4S)-6-(4-chlorophenyl)-1-methyl-4H-benzo[c]isoxazolo[4,5-e]azepin-4-yl)acetamide were dosed orally in dogs at 2 mg/Kg. Both forms (amorphous and monohydrate Form A) were suspended in Methylcellulose (0.4 mg/mL in 0.5% MC). The objective was to compare the pharmacokinetic profiles of both forms in dogs using a crossover study design in which the same dogs were dosed sequentially with amorphous and monohydrate crystalline Form A with a washout period in between. Results are summarized below.

TABLE 9

Plasma concentration and pharmacokinetic parameters of amorphous form of 2-((4S)-6-(4-chlorophenyl)-1-methyl-4H-benzo[c]isoxazolo[4,5-e]azepin-4-yl)acetamide following single oral dose to male beagle dog at 2 mg/Kg.

| Time (h) | D101 | D102 | D103 | D104 | D105 | D106 | Mean | ± | SD | CV(%) |
|---|---|---|---|---|---|---|---|---|---|---|
| 0 | BQL | BQL | BQL | BQL | BQL | BQL | NC | ± | NC | NC |
| 0.25 | 85.7 | 90.1 | 313 | 133 | 126 | 381 | 188 | ± | 126 | 67.1 |
| 0.5 | 482 | 390 | 589 | 444 | 341 | 581 | 471 | ± | 100 | 21.3 |
| 1 | 609 | 646 | 609 | 672 | 705 | 706 | 658 | ± | 43.9 | 6.68 |
| 2 | 596 | 444 | 621 | 555 | 623 | 621 | 577 | ± | 70.0 | 12.1 |
| 4 | 455 | 451 | 681 | 537 | 487 | 558 | 528 | ± | 86.4 | 16.4 |
| 6 | 339 | 230 | 308 | 308 | 263 | 288 | 289 | ± | 38.4 | 13.3 |
| 8 | 240 | 214 | 255 | 241 | 172 | 268 | 232 | ± | 34.3 | 14.8 |
| 12 | 157 | 134 | 173 | 154 | 114 | 184 | 153 | ± | 25.5 | 16.7 |
| 24 | 61.6 | 49.0 | 87.8 | 75.8 | 33.8 | 76.2 | 64.0 | ± | 20.0 | 31.2 |
| $C_{max}$ (ng/mL) | 609 | 646 | 681 | 672 | 705 | 706 | 670 | ± | 37.3 | 5.56 |
| $T_{max}$ (h) | 1.00 | 1.00 | 4.00 | 1.00 | 1.00 | 1.00 | 1.50 | ± | 1.22 | 81.6 |
| $T_{1/2}$ (h) | 8.31 | 7.86 | 10.17 | 9.21 | 6.82 | 9.17 | 8.59 | ± | 1.18 | 13.7 |
| $AUC_{0-last}$ (ng · h/mL) | 5370 | 4560 | 6220 | 5540 | 4610 | 6060 | 5393 | ± | 701 | 13.0 |
| $AUC_{0-inf}$ (ng · h/mL) | 6110 | 5120 | 7510 | 6550 | 4950 | 7070 | 6218 | ± | 1033 | 16.6 |
| $MRT_{0-last}$ (h) | 7.59 | 7.45 | 7.73 | 7.73 | 6.48 | 7.69 | 7.45 | ± | 0.48 | 6.51 |
| $MRT_{0-inf}$ (h) | 11.02 | 10.48 | 13.04 | 12.28 | 8.32 | 11.90 | 11.17 | ± | 1.67 | 14.9 |

TABLE 10

Plasma concentration and pharmacokinetic parameters of monohydrate Form A of 2-((4S)-6-(4-chlorophenyl)-1-methyl-4H-benzo[c]isoxazolo[4,5-e]azepin-4-yl)acetamide following single oral dose to male beagle dog at 2 mg/Kg.

| Time (h) | D101 | D102 | D103 | D104 | D105 | D106 | Mean | ± | SD | CV(%) |
|---|---|---|---|---|---|---|---|---|---|---|
| 0 | BQL | BQL | BQL | BQL | BQL | BQL | NC | ± | NC | NC |
| 0.25 | 126 | 166 | 147 | 49.2 | 4.96 | 108 | 100 | ± | 61.5 | 61.4 |
| 0.5 | 333 | 296 | 410 | 292 | 257 | 390 | 330 | ± | 59.9 | 18.2 |
| 1 | 542 | 465 | 615 | 419 | 522 | 569 | 522 | ± | 70.9 | 13.6 |
| 2 | 483 | 482 | 558 | 459 | 549 | 541 | 512 | ± | 42.1 | 8.23 |
| 4 | 414 | 359 | 506 | 332 | 546 | 451 | 435 | ± | 83.0 | 19.1 |
| 6 | 273 | 257 | 314 | 226 | 321 | 275 | 278 | ± | 35.6 | 12.8 |
| 8 | 209 | 171 | 240 | 165 | 253 | 248 | 214 | ± | 39.1 | 18.2 |
| 12 | 140 | 113 | 190 | 114 | 161 | 188 | 151 | ± | 34.4 | 22.8 |
| 24 | 56.3 | 42.9 | 95.0 | 61.0 | 69.0 | 78.1 | 67.1 | ± | 18.1 | 27.0 |
| No. points of $t_{1/2}$ | 3 | 3 | 3 | 3 | 4 | 3 | — | ± | — | — |
| $C_{max}$ (ng/mL) | 542 | 482 | 615 | 459 | 549 | 569 | 536 | ± | 57.2 | 10.7 |
| $T_{max}$ (h) | 1.00 | 2.00 | 1.00 | 2.00 | 2.00 | 1.00 | 1.50 | ± | 0.55 | 36.5 |
| $T_{1/2}$ (h) | 8.60 | 8.14 | 11.97 | 11.58 | 8.31 | 9.57 | 9.70 | ± | 1.69 | 17.4 |
| $AUC_{0-last}$ (ng · h/mL) | 4650 | 4040 | 5850 | 3960 | 5390 | 5460 | 4892 | ± | 793 | 16.2 |
| $AUC_{0-inf}$ (ng · h/mL) | 5350 | 4540 | 7490 | 4980 | 6220 | 6540 | 5853 | ± | 1098 | 18.8 |
| $MRT_{0-last}$ (h) | 7.74 | 7.34 | 8.38 | 8.01 | 7.93 | 8.32 | 7.95 | ± | 0.39 | 4.84 |
| $MRT_{0-inf}$ (h) | 11.49 | 10.49 | 15.59 | 14.70 | 11.66 | 13.18 | 12.85 | ± | 1.99 | 15.5 |

Both the amorphous solid and the monohydrate crystalline Form A show similar pharmacokinetic profiles and low inter-individual variability. These are favorable and unexpected properties of the monohydrate crystalline Form A.

While have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. Crystalline Form A of 2-((4S)-6-(4-chlorophenyl)-1-methyl-4H-benzo[c]isoxazolo[4,5-e]azepin-4-yl)acetamide, wherein the crystalline form is characterized by at least three x-ray powder diffraction peaks at 2Θ angles selected from 4.73°, 18.09°, 18.48°, 18.80°, 19.70°, and 25.17°.

2. The crystalline Form A of claim 1, wherein the crystalline form is characterized by at least four x-ray powder diffraction peaks at 2Θ angles selected from 4.73°, 18.09°, 18.48°, 18.80°, 19.70°, and 25.17°.

3. The crystalline Form A of claim 1, wherein the crystalline form is characterized by at least five x-ray powder diffraction peaks at 2Θ angles selected from 4.73°, 18.09°, 18.48°, 18.80°, 19.70°, and 25.17°.

4. The crystalline Form A of claim 1, wherein the crystalline form is characterized by x-ray powder diffraction peaks at 2Θ angles 4.73°, 18.09°, 18.48°, 18.80°, 19.70°, and 25.17°.

5. The crystalline Form A of claim 1, wherein the crystalline form is characterized by x-ray powder diffraction peaks at 2Θ angles 4.73°, 9.42°, 12.91°, 18.09°, 18.48°, 18.80°, 19.70°, 21.42°, and 25.17°.

6. The crystalline Form A of claim 1, wherein the crystalline form is characterized by x-ray powder diffraction peaks at 2Θ angles 4.73°, 8.11°, 9.42°, 12.91°, 14.10°, 14.97°, 18.09°, 18.48°, 18.80°, 19.70°, 21.42°, and 25.17°, 26.07°, and 26.53°.

7. The crystalline Form A of claim 1, wherein the crystalline Form is a hydrate.

8. The crystalline Form A of claim 1, wherein the crystalline Form is a monohydrate.

9. A pharmaceutical composition comprising the crystalline form of claim 1; and a pharmaceutically acceptable carrier or diluent.

10. A process for preparing monohydrate crystalline Form A of 2-((4S)-6-(4-chlorophenyl)-1-methyl-4H-benzo[c]isoxazolo[4,5-e]azepin-4-yl)acetamide, the process comprising:
    forming the monohydrate crystalline Form A from a solution comprising amorophous 2-((4S)-6-(4-chlorophenyl)-1-methyl-4H-benzo[c]isoxazolo[4,5-e]azepin-4-yl)acetamide and water; or from a mixture comprising amorophous 2-((4S)-6-(4-chlorophenyl)-1-methyl-4H-benzo[c]isoxazolo[4,5-e]azepin-4-yl)acetamide,
    and a combination of water and organic solvent.

11. The process of claim 10, wherein the combination of water and organic solvent is selected from ethanol/water, isopropanol/water, tetrahydrofuran/water, acetone/water, methanol/water, and acetonitrile/water.

12. The process of claim 10, wherein the combination of water and organic solvent is ethanol/water.

13. The process of claim 10, wherein the combination of water and organic solvent is a 60:40 mixture of ethanol/water.

* * * * *